(12) United States Patent
Weinberg et al.

(10) Patent No.: US 6,934,583 B2
(45) Date of Patent: Aug. 23, 2005

(54) IMPLANTABLE LEAD AND METHOD FOR STIMULATING THE VAGUS NERVE

(75) Inventors: Lisa P. Weinberg, Moorpark, CA (US); Paul A. Levine, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 424 days.

(21) Appl. No.: 10/000,333

(22) Filed: Oct. 22, 2001

(65) Prior Publication Data

US 2003/0078623 A1 Apr. 24, 2003

(51) Int. Cl.⁷ .............................................. A61N 1/362
(52) U.S. Cl. ......................................................... 607/9
(58) Field of Search ............................. 607/4–28, 122, 607/123

(56) References Cited

U.S. PATENT DOCUMENTS

| | | | |
|---|---|---|---|
| 4,289,144 A | * | 9/1981 | Gilman |
| 4,643,201 A | | 2/1987 | Stokes .......................... 128/786 |
| 5,243,980 A | | 9/1993 | Mehra ............................. 607/6 |
| 5,330,507 A | * | 7/1994 | Schwartz |
| 5,354,318 A | | 10/1994 | Taepke .......................... 607/22 |
| 5,356,425 A | | 10/1994 | Bardy et al. ................... 607/14 |
| 5,411,025 A | | 5/1995 | Webster, Jr. ................. 128/642 |
| 5,466,254 A | | 11/1995 | Helland ........................ 607/123 |
| 5,476,483 A | | 12/1995 | Bornzin et al. ................ 607/17 |
| 5,507,784 A | | 4/1996 | Hill et al. ....................... 607/14 |
| 5,578,061 A | | 11/1996 | Stroetmann et al. ............. 607/4 |
| 5,782,239 A | | 7/1998 | Webster, Jr. ................. 128/642 |
| 5,916,239 A | | 6/1999 | Geddes et al. ................. 607/14 |
| 5,968,040 A | | 10/1999 | Swanson et al. ............... 606/41 |
| 6,006,134 A | | 12/1999 | Hill et al. ........................ 607/9 |
| 6,157,862 A | * | 12/2000 | Brownlee et al. |
| 6,201,994 B1 | | 3/2001 | Warman et al. .............. 607/123 |
| 6,295,475 B1 | | 9/2001 | Morgan ........................ 607/122 |
| 6,345,198 B1 | * | 2/2002 | Mouchawar et al. |
| 6,697,677 B2 | * | 2/2004 | Dahl et al. ................... 607/128 |

FOREIGN PATENT DOCUMENTS

| | | | |
|---|---|---|---|
| EP | 0993840 A1 | 4/2000 | ............ A61N/1/05 |
| FR | 2801509 A | 6/2001 | ............ A61N/1/05 |
| WO | WO 00/78391 A1 | 12/2000 | .......... A61N/1/365 |
| WO | WO 01/00273 A1 | 1/2001 | ............ A61N/1/05 |

OTHER PUBLICATIONS

Schauerte, P. et al., Transvenous Parasympathetic Cardiac Nerve Stimulation for Treatment of Tachycardic Atrial Fibrillation, Tachycarde Rhythmusstörungen, 89:766–773 (2000).

(Continued)

Primary Examiner—Scott M. Getzow

(57) ABSTRACT

Methods and apparatus for stimulating the right vagal nerve within a living body via positioning an electrode portion of a lead proximate to the portion of the vagus nerve where the right cardiac branch is located (e.g., near or within an azygos vein, or the superior vena cava near the opening of the azygos vein) and delivering an electrical signal to an electrode portion adapted to be implanted therein. Stimulation of the right vagus nerve and/or the cardiac branch thereof act to slow the atrial heart rate. Exemplary embodiments include deploying an expandable or self-oriented electrode (e.g., a basket, an electrode umbrella, and/or an electrode spiral electrode, electrode pairs, etc). Various dedicated and single-pass leads are disclosed, as well as, various electrodes, and stabilization means. The methods include preserving sinus rhythm, avoiding asystole, preserving A-V synchrony, automatically determining parameter combinations that achieve these features, and further (in one embodiment) automatically determining parameter combinations achieve these features and reduce current drain.

15 Claims, 19 Drawing Sheets

OTHER PUBLICATIONS

Bilgutay, Aydin M., et al., Vagal Tuning, Journal of Thoracic and Cardiovascular Surgery, vol. 56, No. 1, pp: 71–82 (Jul. 1968).

Scherlag, M.D., Michael A., et al., Transvenous Parasympathetic Cardiac Nerve Stimulation: A New Approach for Sinus Rate Control, PACE, vol. 22, No. 4, Part II, Abstract Session I, (Listed date, Apr. 1999) and (Publically disclosed on May 13, 1999).

Cooper, Terry B., et al., Neural Effects on Sinus Rate and Atrioventricular Conduction Produced by Electrical Stimulaiton from a Transvenous Electrode Catheter in the Canine Right Pulmonary Artery, Circulation Research, vol. 46, No. 1, pp: 48–57, (Jan. 1980).

Schauerte, Patrick MD, et al., "Catheter Stimulation of Cardiac Parasympathetic Nerves in Humans", Circulation, pp: 2430–2435 (Nov. 13, 2001).

* cited by examiner

FIG. 16
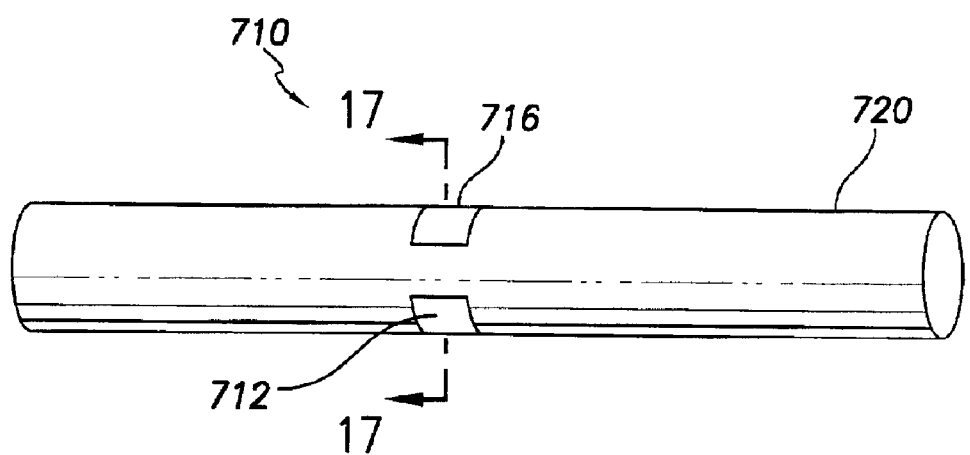
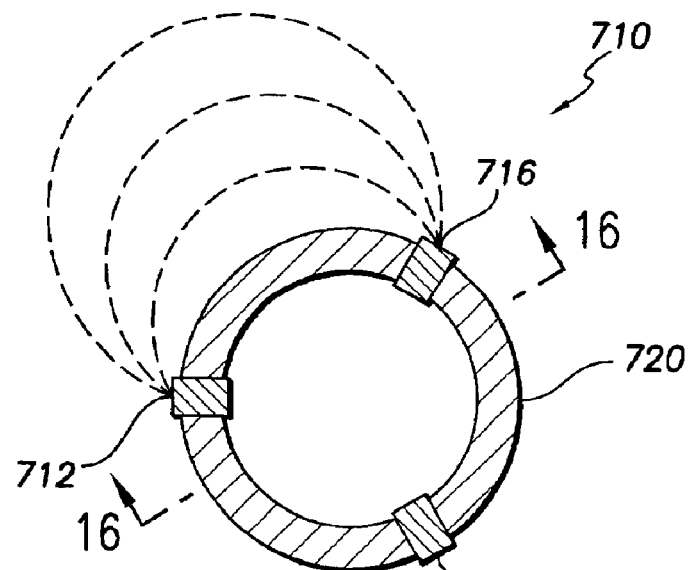
FIG. 17

IMPLANTABLE LEAD AND METHOD FOR STIMULATING THE VAGUS NERVE

FIELD OF THE INVENTION

The present invention generally relates to methods and systems for providing cardiac pacing therapy. More particularly, the invention concerns methods and implantable stimulation leads, systems and methods for stimulating the right vagus nerve.

BACKGROUND

The vagus nerve is a member of a group of nerves commonly referred to as the cranial nerves. Scientifically, the vagus nerve has been designated as the tenth cranial nerve. There are two of these mixed nerves that act to provide both motor and sensory functions. Each vagus nerve contains both somatic and autonomic branches, however within the body the autonomic function predominates. Vagus nerves are parasympathetic in nature making up 75% of all parasympathetic fibers passing to the thoracic and abdominal regions of the body. As is the case with most nerves, vagus nerves contain both efferent fibers, carrying impulses from its origin in the medulla obligata of the brain to a tissue or visceral organ, as well as afferent fibers, which carry the impulse from the organ back to the brain itself. With vagus nerves, 80% of the fibers are afferent as opposed to efferent. This aids in their active response to the many reflex actions in the body during parasympathetic control. As a whole, the two vagus nerves are very large and work to stimulate a great number of tissues in the body. Vagal stimulation works to innervate the heart, lungs, esophagus, stomach, small intestine, liver, gall bladder, as well as the upper portions of the ureters.

As the vagus nerves become stimulated, the hormone acetylcholine is released at the vagal endings. Therefore, vagus nerves are said to be cholinergic (a term signifying the hormone by which it secretes). This is in contrast with adrenergic systems which cause the release of epinephrine and norepinephrine. It is the release of acetylcholine, rather than the passing of nerve impulses that directly initiates the specific response within the organ.

In the heart, parasympathetic vagus nerves are distributed mainly to the SA node and the AV node. Although stimulation does occur to both atrial and ventricular muscle, the majority of its action occurs in the nodal areas. Release of acetylcholine to these areas results in both a decrease in the rate or rhythm (e.g., the degree of heart rate variability is heavily influenced by vagal stimulation) of the SA node, as well as a decrease in the cardiac impulse transmission into the ventricles. Consequences of these actions include decreases in heart rate, cardiac output, ventricular contraction, arterial blood pressure, as well as overall ventricular pumping.

More specifically, the right vagus innervates the S-A node, the atrial muscle and, to a much lesser degree, the A-V node. The left vagus nerve innervates the S-A node and atrial muscle to a lesser degree than it innervates the A-V node. It is well known to physiologists that stimulation of the right vagus nerve predominately slows the S-A node rate and thereby reduces heart rate. Stimulation of the left vagus nerve produces some slowing of the S-A node, prolongation of A-V conduction and partial or total A-V block.

Regarding left vagal stimulation, U.S. Pat. No. 5,916,239, entitled "Method and apparatus using vagal stimulation for control of ventricular rate during atrial fibrillation", to Geddes, et al., issued Jun. 29, 1999 ('239 patent), states that "low-frequency left vagal stimulation causes a dramatic shortening of the duration of the atrial monophasic action potential, indicating shortening of the atrial refractory period" and that "[a]lthough the left vagus nerve affects atrial rate to a lesser degree, transmission of excitation across the A-V node is largely regulated by the left vagus nerve" (col. 1, I. 59–61). The '239 patent also discloses that "atrial fibrillation can be allowed to persist and that stimulation of the left vagus nerve, as opposed to the right vagus, is necessary and sufficient to effectively control the ventricular rate during atrial fibrillation" (col. 2, I. 55–58). However, the current theory on atrial fibrillation is NOT to let it persist, since it can cause poor hemodynamics and permanent remodeling of the heart, but instead to terminate it quickly. Thus, the present invention is directed towards controlling the right vagus nerve, particularly those affecting the cardiac branch, so that the Sinus Node, the associated conduction system and perhaps even the length of atrial refractory, can be slowed.

The '239 patent discloses a device having a first pair of electrodes in the right ventricle for providing ventricular pacing and sensing, a second pair of electrodes in the right atrium for atrial pacing and sensing, and a third pair of electrodes "attached or adjacent to the left vagus nerve" (col. 4, I. 54–55) for stimulating left vagus nerve and controlling ventricular rate. The '239 patent discloses "a catheter electrode in the right atrium and ventricle and another electrode on the left vagus nerve" (col. 11, I. 33–35). The '239 patent further states that "the principle can be applied using catheter electrodes" by using "a catheter electrode in the right pulmonary artery to stimulate the left vagus nerve, as described by Cooper et al. (Circ. Res. 1980, 46:48–57)" (col. 11, I. 35–38).

The '239 patent also refers to a paper by Bilgutay et al. (*J. Thoracic Cardiovas. Surg.* 56(1):71–82, July, 1968) In his experiments, Bilgutay et al. indicated that the right vagus nerve was stimulated [in the neck of dogs using a nerve cuff] because its distribution is known to be mostly to the sinoatrial node area, and further that stimulation of the left vagus nerve (in a dog with complete heart block) slowed the ventricular rate and suggest that this may be effective in nodal tachycardias. Bilgutay defined the optimal heart rate as the slowest heart rate that could be attained by vagal stimulation without causing A-V dissociation or complete heart block. (col. 2, I. 4–30). That is, too much stimulation (e.g., amplitude, pulse width or frequency) can cause A-V block, decreased cardiac output and decreased coronary flow. Bilgutay et. al experimented with various currents of different frequencies, pulse shapes and pulse widths, and noted that 10 pps and 0.2 msec pulse duration with increasing only the amplitude of the current attained very predictable changes in rate.

An International Patent Application published under the Patent Cooperation Treaty (WO 01/00273 A1; PCT/US00/17222), entitled "Devices and methods for vagus nerve stimulation", publication date Jan. 4, 2001 ('273 application), discloses devices and methods for "electrically-induced and pharmaceutically prolonged cardiac asystole" (p. 1, I. 7–8) for controlling heart beats during cardiac surgery, and more particularly, during coronary artery by-pass surgery (CABG) when anastomatic formation is readily disrupted by a beating heart A stated object of the '273 application is to induce asystole by applying an electrical stimulus to the vagus nerve (p. 3, I. 29–31). FIGS. 2A–B, 3A–3E, 4A–4F, and 5A–5B show electrodes for electrically inducing asystole.

These Figures and their corresponding description are incorporated by reference herein for all purposes.

According to the '273 application, "[t]he chronotropic effect of vagal nerve stimulation in the absence of pharmacological potentiation includes a very brief initial pause followed by 'vagal escape' beats and transient bradycardia" and "[v]agus nerve stimulation alone does not produce controlled asystole" (p. 9, I. 10–14). Therefore, the '273 application relies on a combination of electrical stimulation and a pharmacological composition to produce controlled asystole. Based on the work of Bilgutay et al. (above), it is believed that electrical stimulation of the vagus nerves to the point of asystole is hemodyanmically deleterious and should be avoided.

To deliver electrical stimulation to the vagus nerve, the '273 application discloses implanting a percutaneous catheter or an electrode probe in "the internal jugular vein, trachea, esophagus, or a combination thereof" (p. 9, I.7–30). The electrodes disclosed in the '273 application generally have a basket, balloon or umbrella configuration, wherein "the optimal number of wires can vary depending upon the circumstances" and wherein "[e]ach wire is an independent electrode, electrically exposed only on its outer service at the point where it makes contact with the wall of the internal jugular vein, trachea, or esophagus" (p. 10, I. 16–20). Further, the '273 application states that a bipolar electric field can be established "between electrodes on individual devices in separate anatomical structures" such as, "a balloon, basket or umbrella . . . in the jugular vein, while another electrode is on a balloon, basket or umbrella in the trachea or in the esophagus" (p. 10, I. 33–35; p. 11, I. 1–2).

Intravenous catheters disclosed by the '273 application have "a distally disposed electrode means that can be expanded in the internal jugular vein so as to press up against the internal wall of the internal jugular vein and force contact between an electrode and the blood vessel wall" (p. 15, I. 6–9). This arrangement "allows electrical current and electrical fields to pass through the thin wall of the internal jugular vein to stimulate the vagus nerve, which lies immediately adjacent to the internal jugular vein" (p. 15, I. 9–12). According to the '273 application, for purposes disclosed therein, the "electrode means can be added to any intravascular catheter device known to one of skill in the art . . . including the Swan Ganz catheter" (p. 15, I. 12–14).

The '273 application also discloses, a cardiac monitoring device (20) connected to a patient by a connection means (21) (p. 13, I. 4–6) and a cardiac pacer device (60) for pacing the heart out of asystole and a pacer to patient connecting means (61) (p. 13, I. 35–36; p. 14, I. 1). Further, to prevent inadvertent cardiac stimulation "[t]he cardiac pacer output can be 'off' whenever the vagal stimulator output is 'on'" (p. 14, I. 6–7).

Typically in the past, nerve stimulating electrodes were of the cuff-type or impalement-type. These electrodes can potentially cause irreversible nerve damage due to swelling or direct mechanical damage to the nerve, and such placement is usually performed through very invasive surgery, which produces a high risk to nerve damage.

More recently, transvenous-type electrodes have been in use, typically "floating" ring or surface electrodes along a lead body, such as that taught in U.S. Pat. No. 6,006,134 ('134 patent), entitled "Method and device for electronically controlling the beating of a heart using venous electrical stimulation of nerve fibers", to Hill et al., issued Dec. 21, 1999. Briefly, the '134 patent discloses advancing a lead having an array of electrodes into a patient's vascular system wherein a user must selectively employ electrodes within the array to properly direct electrical pulses applied to the electrodes to desired nerve fibers. The '134 patent discloses "stimulating" (i.e., initiating a heartbeat) and "destimulating" (i.e., stopping or arresting the heartbeat). The '134 patent also discloses insertion of a selectively employed electrodes catheter "into the internal jugular vein for stimulation of the right and left vagal nerve bundle . . . into the very high internal jugular vein to stimulate the hypoglossal nerve and/or into the very low jugular vein or SVC to stimulate the phrenic nerve for respiratory control" . . . and further states "into the azygos or accessory hemiazygous veins to stimulate the sympathetic nerves for increasing heart rate" (col. 8, I. 519–23).

A known problem with these types of surface electrodes is that they can make poor contact with tissue if they are merely lying within a vessel, or adjacent a vessel. Furthermore, the orientation of the electrodes for the best contact (i.e., lowest thresholds) often has to be determined by the physician.

What is needed is an implantable stimulation lead having an electrode portion capable of making good contact with the portion of the right vagus nerve with leads to the heart for stimulating parasympathetic nerves for decreasing the atrial heart rate (and preferably, without stimulating the phrenic nerve which can evoke undesirable diaphragmatic stimulation), such as the cardiac branch site where the right vagus nerve enters into the right atrium at the level of the SVC/RA junction, or just below the azygos vein; and a method of positioning of such a lead into the azygos or hemizygos veins and providing techniques for automatically determining an appropriate stimulation level.

What is further needed is a method of automatically and gradually adapting the vagal stimulation until a desired reduction in atrial heart rate is achieved, while preserving sinus rhythm (i.e., a normal cardiac rate set by the sinus node, normally between 60 and 100 bpm) and maintaining A-V synchrony, and further capable of providing backup A-V sequential support pacing in the event that asystole occurs.

And finally, a single-pass implantable stimulation lead is needed (one that can that can stimulate the desired portion of the right vagus nerve and stimulating the right atrium, the right ventricle and/or the left ventricle) to simplify the implant procedure: a lead that can provide an orientation suitable for implantation in a patient's right azygos vein, azygos arch, and/or hemiazygos veins.

SUMMARY

An exemplary method described herein includes stimulating the right vagal nerve within a living body via positioning an electrode portion of a lead within an azygos vein and delivering an electrical signal to the electrode portion. In this exemplary method, the positioning optionally includes deploying an electrode basket, an electrode umbrella, and/or an electrode spiral. Various leads described herein allow for determining the orientation of the electrode portion of the lead with respect to the azygos vein prior to positioning and/or determining the orientation of the electrode portion of the lead with respect to the right vagus nerve, and/or the cardiac branch thereof, prior to positioning. Stimulation of the right vagus nerve and/or the cardiac branch thereof optionally acts to slow heart rate.

Also described herein are exemplary apparatus for stimulating a right vagus nerve within a living body. One exemplary apparatus includes a lead having an electrode portion wherein the electrode portion is positionable within a vein of the living body. According to this exemplary apparatus, the vagus nerve is the right vagus nerve and/or a cardiac branch of a vagus nerve and the vein includes the azygos vein. The delivery of an electrical signal to the electrode portion cause stimulation of the right vagus nerve, which in turn can slow the heart rate.

In another exemplary apparatus, a lead includes a side arm, which comprises an electrode portion. A side arm can help determine orientation of an electrode portion with respect to a vein prior to positioning of the electrode portion in the vein. In this exemplary apparatus, the electrode portion includes, for example, an electrode basket, an electrode umbrella, an electrode spiral, hooks, tines, and/or wiggles. In a variation of this exemplary apparatus, the lead includes more than one electrode portion. In this variation, an additional electrode portion may be positionable in the vascular system, e.g., a vein, an artery, and/or a chamber of the heart. According to one exemplary apparatus, a lead side arm is positionable in an azygos vein, for example, but not limited to, through the superior vena cava.

Other exemplary apparatus for stimulating a vagus nerve within a living body include a lead comprising an electrode portion wherein the electrode portion is positionable within a vein of the living body and comprises an electrode basket portion, an electrode umbrella portion and/or an electrode spiral portion. Such exemplary apparatus optionally have more than one such electrode portion. These particular exemplary apparatus are suited for stimulation of the right vagus nerve and/or the right cardiac branch thereof and suited for positioning in the azygos vein. As already mentioned, stimulation of the right vagus nerve and/or the cardiac branch thereof can slow heart rate. Several of the exemplary apparatus described herein can also be used to stimulate the left vagus nerve and/or the left cardiac branch thereof.

Yet another exemplary apparatus for stimulating a vagus nerve within a living body includes a lead comprising a side arm wherein the side arm is positionable within a vein of the living body and optionally extendable. Extendable includes, but is not limited to, telescopic and/or angular extendability.

According to this exemplary apparatus, the extendable side arm optionally includes an electrode portion positionable in an azygos vein wherein the positionable electrode portion can carry an electrical signal capable of stimulating the vagus nerve and slowing heart rate.

In one embodiment, the method applies vagal stimulation of varying intensities until a desired reduced heart rate is achieved while maintaining or preserving sinus rhythm (thereby avoiding asystole).

In another embodiment, the method includes steps for automatically determining a parameter combination that defines the intensity (i.e., amplitude, pulse width and frequency) that achieves a desired reduced heart rate.

In a further embodiment, the A-V conduction is monitored to ensure that A-V dissociation (e.g., prolongation of the A-V conduction, and/or various degrees of A-V block) does not occur from too high an intensity of vagal stimulation.

And in still another embodiment, the power consumption is monitored and a plurality of parameter combinations that defines the intensity are tested to determine preferred combinations that do not draw too much current drain. Such a method optionally adjusts one or more of frequency, pulse width and/or amplitude of the stimulating. Such adjusting optionally occurs periodically during treatment of tachycardia and/or as part of a pre-treatment calibration sequence.

Advantageously, such methods of vagal stimulation will have a slowing affect on repolarization and refractory periods which will aid in the control of heart rhythms and/or to aid in remodeling of the heart. In particular, control of the vagal tone can enhance tachycardia therapy.

The methods respond to fast atrial rhythms such as pathological sinus tachycardia, atrial flutter, and atrial fibrillation by stimulating the right vagus nerve to slow a patient's heart sinus rhythm without causing A-V dissociation.

The various apparatus and methods described herein, and equivalents thereof, are suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

FIG. 16 is a side view diagram of another embodiment of a lead having an electrode array suitable for use with various leads and/or methods described herein;

FIG. 17 is an axial cross-sectional view diagram of the lead shown in FIG. 16 illustrating the current flow;

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Exemplary Stimulation Device

The techniques described below are intended to be implemented in connection with any stimulation device that is configured or configurable to stimulate or shock a patient's heart.

Figure 1:
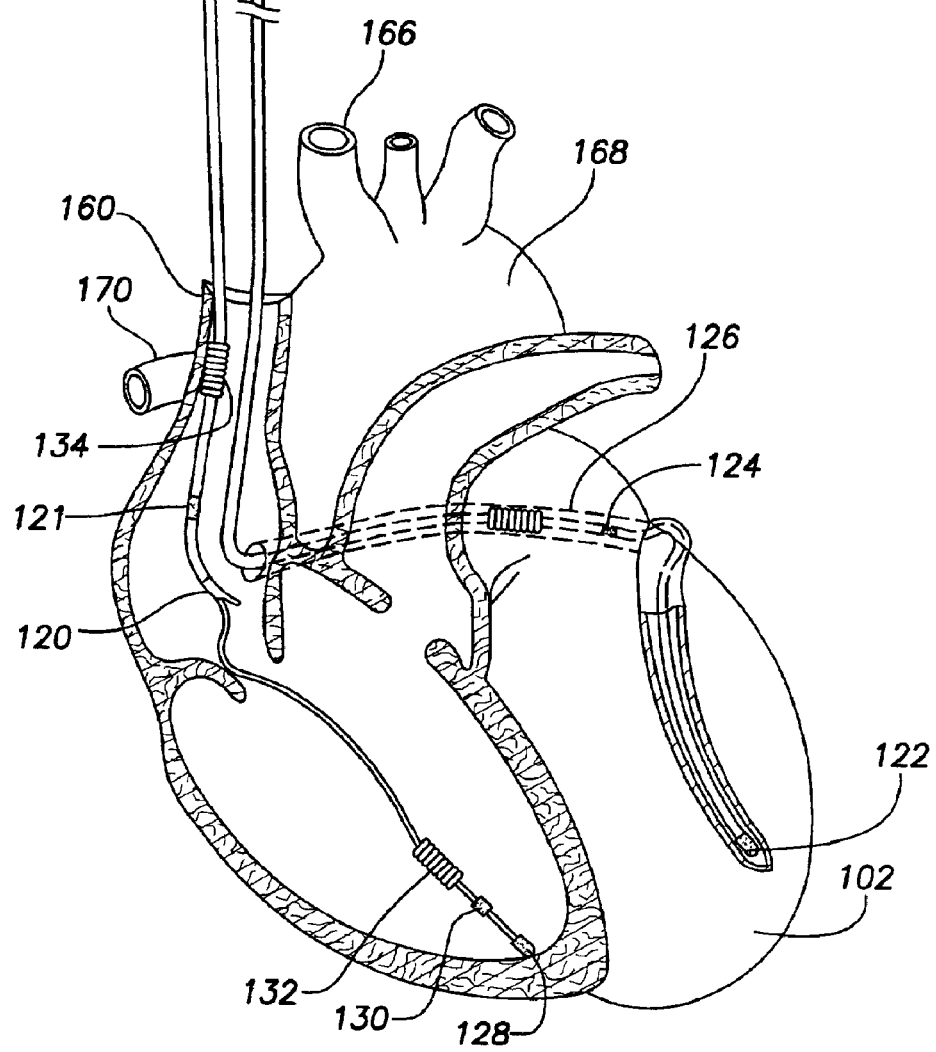
FIG. 1 illustrates two prior art single-pass leads capable of delivering multi-chamber stimulation and shock therapy.

FIG. 1 shows an exemplary stimulation device 100 in electrical communication with a patient's heart 102 by way of three electrical "connections" 104, 106, and 108, suitable for delivering multi-chamber stimulation and shock therapy. While two of the electrical connections (104 and 108) are shown as a single-pass lead, since the present invention is directed in some embodiments towards an improved single-pass lead, it is to be understood that individual leads could also be used to describe the fundamentals of multi-chamber stimulation. Accordingly, the term electrical "connections" will be used herein to describe the system that makes contact with an electrode, whether it is by a single-pass lead or an individual lead.

To sense atrial cardiac signals and to provide right atrial chamber stimulation therapy, stimulation device 100 is coupled to an implantable right atrial electrical connection 104, coupled to at least an atrial tip electrode 120 and optionally an atrial ring electrode 121, which typically is implanted in the patient's right atrial appendage.

Stimulation device 100 is also shown in electrical communication with the patient's heart 102 by way of an implantable right ventricular connection 108 having, in this implementation, a right ventricular tip electrode 128, a right ventricular ring electrode 130, a right ventricular (RV) coil electrode 132, and an SVC coil electrode 134. Accordingly, the right ventricular connection 108 is capable of sensing or receiving cardiac signals, and delivering stimulation in the form of pacing and shock therapy to the right ventricle.

To sense left atrial and ventricular cardiac signals and to provide left chamber pacing therapy, stimulation device 100 is coupled to a single-pass coronary sinus connection 106, that is, a lead designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus connection 106 is designed to receive atrial and ventricular cardiac signals and to deliver left ventricular pacing therapy using at least a left ventricular tip electrode 122, left atrial pacing therapy using at least a left atrial ring electrode 124, and shocking therapy using, for example a left atrial coil electrode 126 (or a left ventricular coil electrode, not shown, or both). For a complete description of a coronary sinus lead, the reader is directed to U.S. patent application Ser. No. 09/457,277, filed Dec. 8, 1999, entitled "A Self-Anchoring, Steerable Coronary Sinus Lead" (Pianca et. al), which patent is hereby incorporated herein by reference.

Figure 2:
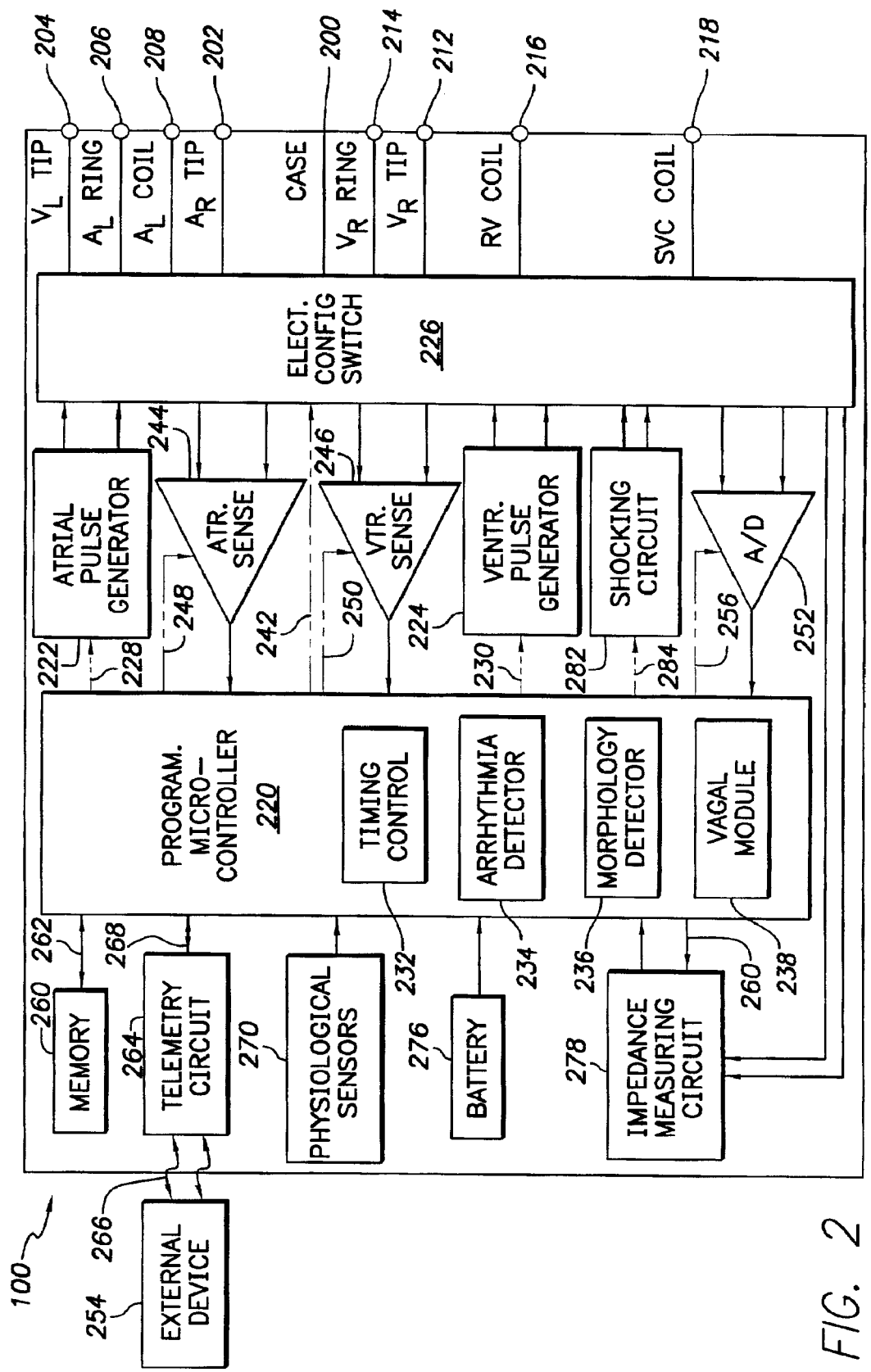
FIG. 2 is a functional block diagram of a multi-chamber implantable stimulation device illustrating basic elements that are configured to provide cardioversion, defibrillation, bradycardia pacing stimulation in four chambers of the heart, in addition to vagal stimulation

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) with cardioversion, defibrillation, and pacing stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 202, 204, 206, 208, 212, 214, 216, and 218 (shown schematically and, for convenience, the names of the electrodes to which they are connected are shown next to the terminals).

To achieve right atrial sensing and pacing, the connector includes at least a right atrial tip terminal ($A_R$ TIP) 202 adapted for connection to the atrial tip electrode 120. To achieve left chamber sensing, pacing, and shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively.

To support right chamber sensing, pacing, and shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

FIG. 2 also shows an atrial pulse generator 222 and a ventricular pulse generator 224 that generate pacing stimulation pulses for delivery by the right atrial connection 104, the coronary sinus connection 106, and/or the right ventricular connection 108 via an electrode configuration switch 226. It is understood that in order to provide stimulation therapy in each of the four chambers of the heart, the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes a vagal module 238 for performing a variety of tasks related to vagal stimulation. This component can be utilized by the stimulation device 100 for determining desirable times to administer various therapies, including timing, frequency of pulse trains, amplitude and pulse duration for vagal stimulation in order to control heart rate. The vagal module 238 may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial connection 104, coronary sinus connection 106, and the right ventricular connection 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart.

Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial connection 104, the coronary sinus connection 106, and the right ventricular connection 108 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V—V Delay, etc.) at which the atrial and ventricular pulse generators, 222 and 224, generate stimulation pulses. In the present invention, physiologic sensors may be optionally utilized to confirm hemodynamic improvement following vagal stimulation.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, and so forth. Another sensor that may be used is one that detects activity variance, wherein an activity sensor is monitored diurnally to detect the low variance in the measurement corresponding to the sleep state.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 $\mu$A), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected. Accordingly, the device 100 employs a lithium iodide and/or silver vanadium oxide batteries.

The stimulation device 100 can further include magnet detection circuitry (not shown), coupled to the microcontroller 220, to detect when a magnet is placed over the stimulation device 100 to perform various test functions of the stimulation device 100 and/or to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (up to 0.5 J), moderate (0.5 J to 10 J), or high energy (11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

While the present invention may be employed in a system that provides cardioversion and defibrillation therapy, it may also be used in a system that only provide vagal stimulation to treat fast arrhythmias together with bradycardia support, i.e., in a pacemaker device.

Anatomy

Figure 3:
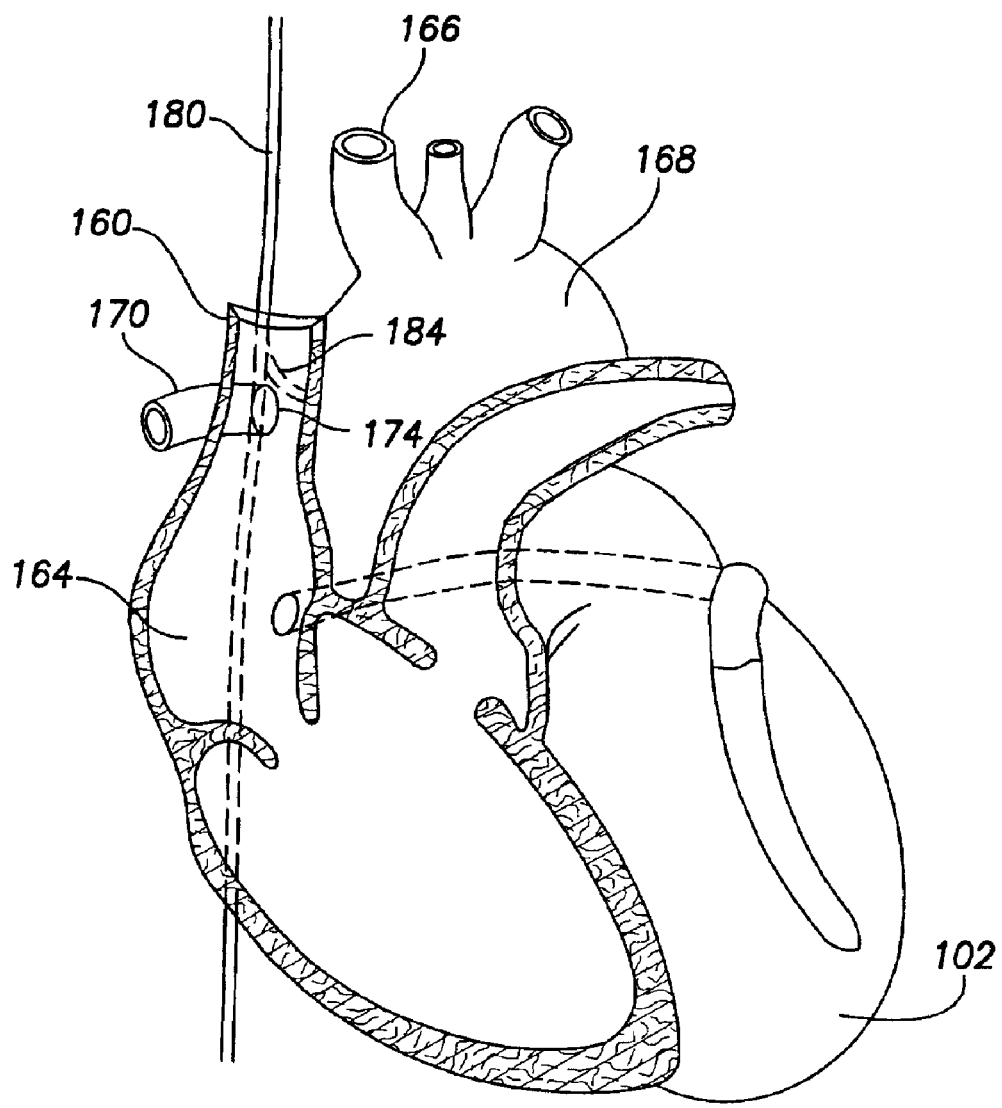
FIG. 3 is an approximate anatomical anterior view diagram of a cross-section of a human heart that shows the azygos vein and the right vagus nerve.

Referring to FIG. 3, a heart 102 and a right vagus nerve 180 are shown. FIG. 3 also shows part of an azygos vein 170, particularly the portion that forms at least part of the "azygos arch" and connects with the heart's superior vena cava 160. The juncture or opening 174 between the azygos vein 170 and the superior vena cava 160 may be considered the end of the azygos vein, where deoxygenated blood enters the superior vena cava 160 en route to the heart's right atrium 164. The azygos vein 170 begins at the union of the right subcostal vein and the right ascending lumbar vein. The azygos vein 170 enters the thorax by passing through the aortic hiatus or by passing through or behind the right crus of the diaphragm. The azygos vein 170 passes upward through the posterior mediastinum near the midline just anterior to the bodies of the thoracic vertebrae or slightly to the right side of the vertebral bodies. At the level of the fourth thoracic vertebra the azygos vein 170 arches anteriorly over the root structures of the right lung to drain into the superior vena cava 160 usually just above the point where the superior vena cava 160 penetrates the pericardium. As the azygos vein 170 passes upward through the posterior mediastinum it lies just to the right of the thoracic duct which is just to the right of the descending aorta.

The hemiazygos vein (not shown) begins at the union of the left ascending lumbar vein and the left subcostal vein. It passes upward into the thorax through the left crus of the diaphragm or through the aortic hiatus. It receives the caudal three or four left posterior intercostal veins and crosses the midline at about the level of the ninth thoracic vertebra to drain into the azygos vein 170. As it crosses the midline it passes dorsal to the aorta, the esophagus and the thoracic duct.

FIG. 3 also shows a general depiction of the heart's aortic arch 168. The aortic arch 168 passes backwards and to the left behind the right half of the munubrium. Crossing the aortic arch 168 anterolaterally are the left phrenic, left vagus, left vagal cardiac branch and left sympathetic cardiac branch (not shown). As the left vagus reaches the inferior border of the aortic arch 168 it gives off the left recurrent laryngeal nerve, which passes backwards around the ligamentum arteriosum, to ascend between the trachea and esophagus. The upper part of the aortic arch 168 gives rise to the brachiocephalic trunk, left common carotid and left subclavian arteries.

Referring again to FIG. 3, the right vagus nerve 180 descends along the innominate artery 166 (also known as the brachiocephalic trunk) and passes medial to the arch of the azygos vein 170 to lie on the right of the trachea. The right vagus nerve 180 also gives rise to a cardiac nerve branch 184 supplying the heart 102. This branch 184 forms a plexus located between the aortic arch 168 and the bifurcation of the trachea. Thus, the right vagus cardiac nerve branch 184 (and/or plexus) passes proximate to the azygos vein 170, in particular, proximate to the arch of the azygos vein 170.

Figure 4:
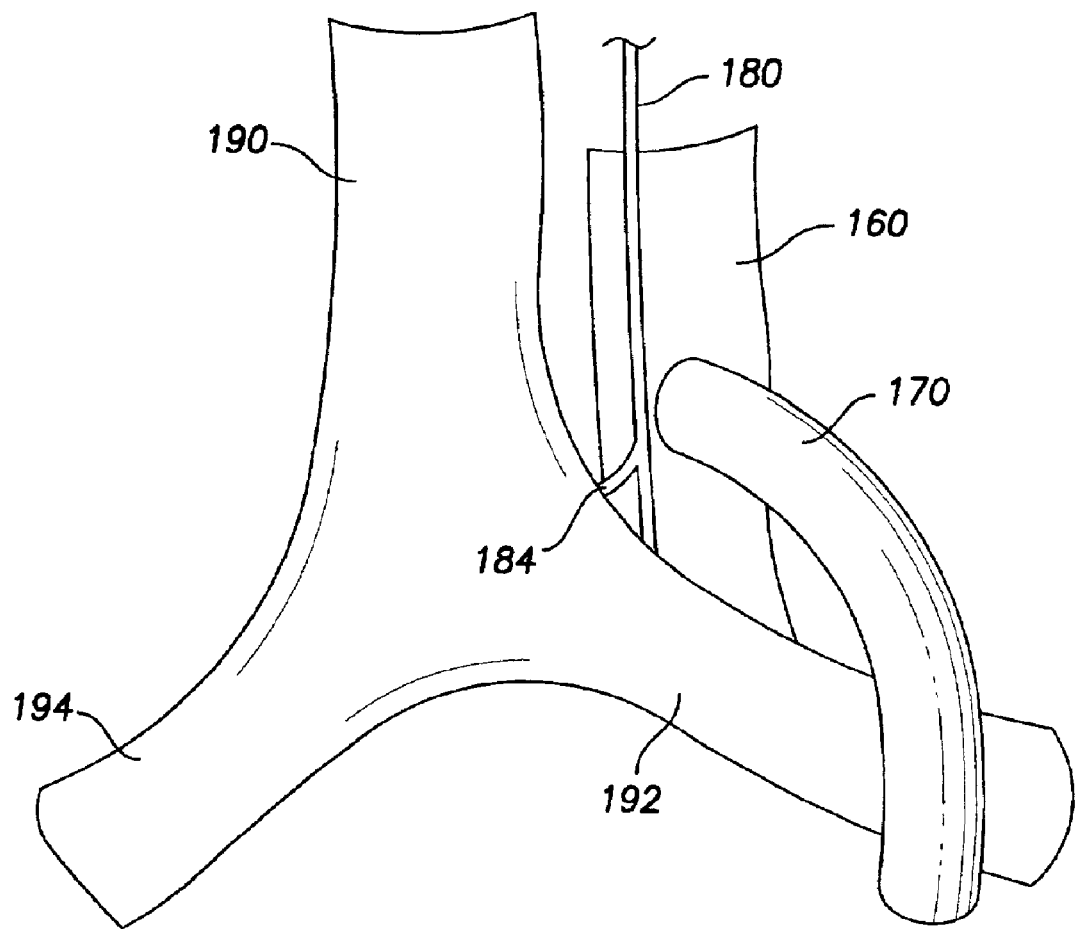
FIG. 4 is an approximate anatomical posterior view diagram showing part of a human trachea, part of the azygos vein, part of the right vagus nerve and part of the superior vena cava.

A posterior illustration of the general anatomy of the aforementioned region appears in FIG. 4. As shown in FIG. 4, the arch of the azygos vein 170 arches over the right bronchus 192 near the bifurcation of the trachea 190. The trachea 190 bifurcates into a right bronchus 192 and a left bronchus 194. Not shown in FIG. 4 are the innominate artery 166 and the right branch of the pulmonary artery, which is medial to the right bronchus 192 and the superior vena cava 160 and anterior to the right vagus nerve 180.

While variation in anatomy typically occurs from one patient to another, the right innominate and the left innominate vein join together and meet the superior vena cava 160 at a vertical point approximately equal to the vertical point where the innominate artery 166 exits the aortic arch 168. From the superior vena cava 160, the left innominate vein passes anterior to the innominate artery 166, in a direction away from the right vagus nerve 180 and towards the left vagus nerve (not shown). As mentioned, the left vagus nerve crosses the aortic arch 168 anterolaterally whereas the right vagus nerve 180 passes posterior to the aortic arch 168 and hence, generally does not contact the surface of the left innominate vein.

For purposes of this discussion, it is the right vagus nerve that is of interest as it is believed to be controlling the Sinus Node and atrial rate, in general, whereas the left vagus nerve is believed to have a greater influence on the A-V Node.

Thus, an exemplary method presented herein includes positioning a lead having at least one electrode in a patient's azygos vein proximate to the right vagus nerve and preferably near the cardiac branch; and stimulating the patient's right vagus nerve and/or right vagal cardiac branch using the at least one electrode. Several exemplary leads are presented herein that include at least one electrode for positioning in a patient's azygos vein and stimulating the patient's right vagus nerve and/or right vagal cardiac branch.

In instances where an azygos vein portion of the lead includes a plurality of electrodes, positioning portions and/ or features alleviate the need for selecting an electrode, or electrodes, amongst the plurality of electrodes to provide for adequate right vagus nerve stimulation.

Leads

FIGS. 5–10 shows six exemplary leads having at least one electrode capable of stimulating a patient's vagus nerve, respectively. Some of these six leads share various features with the leads presented in FIG. 1 and are suitable for use with the device 100 described with reference to FIG. 2.

In particular, the leads shown in FIGS. 5–10 include, in various combinations of connections similar to those presented in FIG. 1, e.g., such as, the right atrial connection 104, the coronary sinus connection 106, and/or the right ventricular connection 108. However, leads shown in FIGS. 5–10 further include a vagal connection 110, that is, a conductor and electrode(s) suitable for stimulating the vagus nerve.

Figure 5:
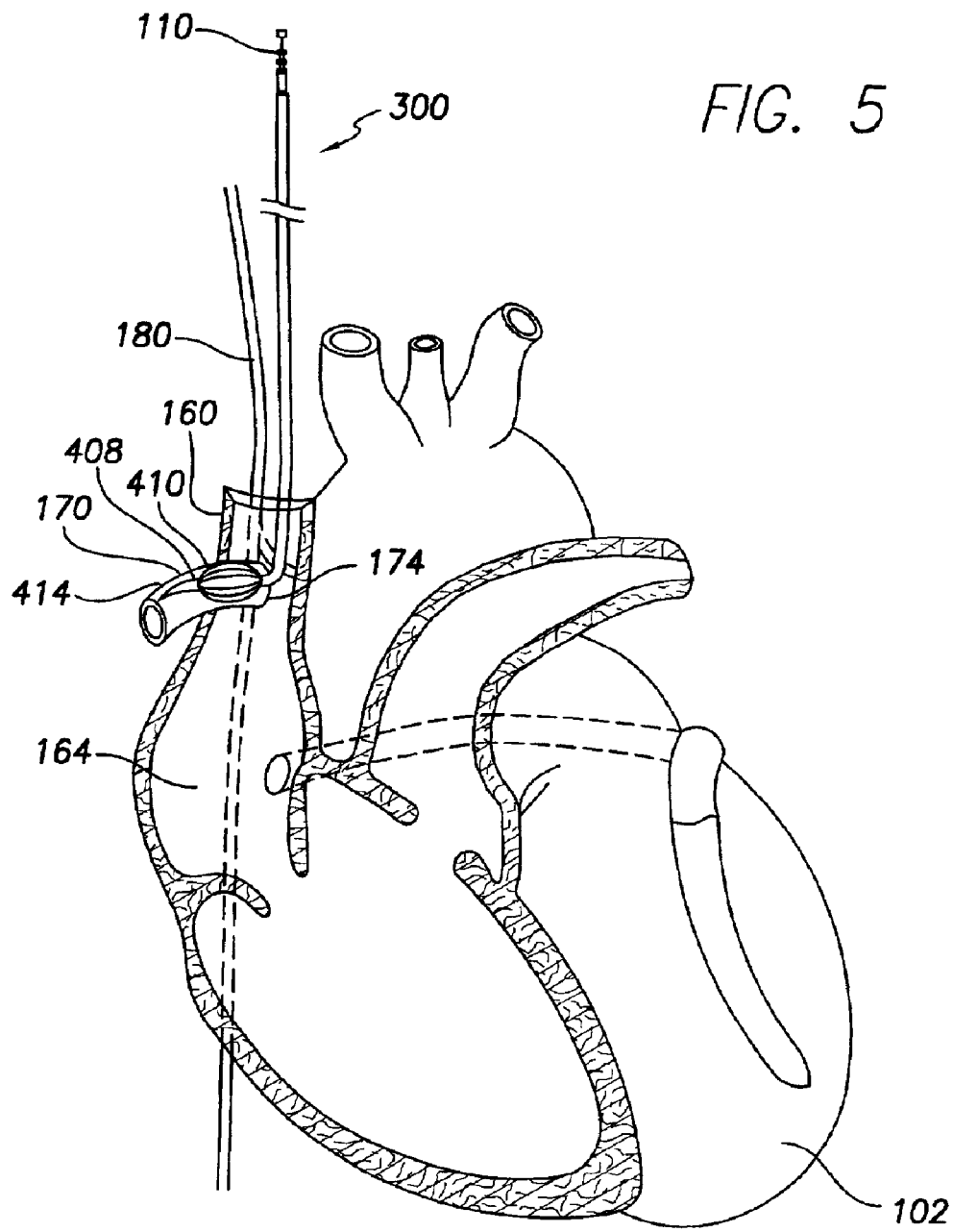
FIGS. 5–10 illustrate six leads, respectively, capable of stimulating the vagal nerve through placement in or near the azygos vein in a location proximate to the vagal nerve and/or the cardiac branch.
Figure 11:
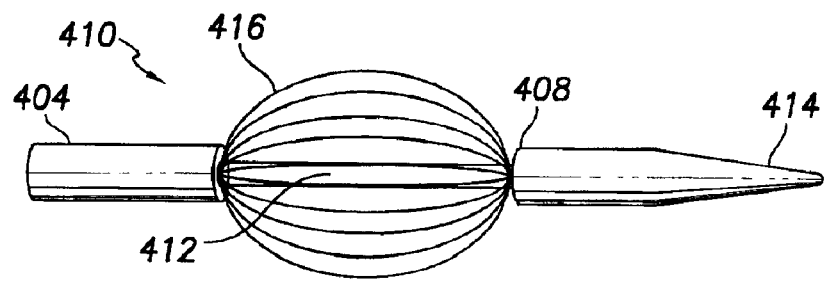
FIG. 11 is a side view diagram of a first embodiment of a deployable electrode in the shape of a basket with a tapered stabilizing portion.

For example, FIG. 5 is a dedicated vagal stimulation lead 310 having a vagal connection 110 (i.e., a proximal connector coupled to a conductor) for electrical contact with a deployable electrode (e.g., a basket electrode in this embodiment), and a distal end 408 having a stabilizing tail portion 414, as described in more complete detail in conjunction with FIG. 11.

Figure 6:
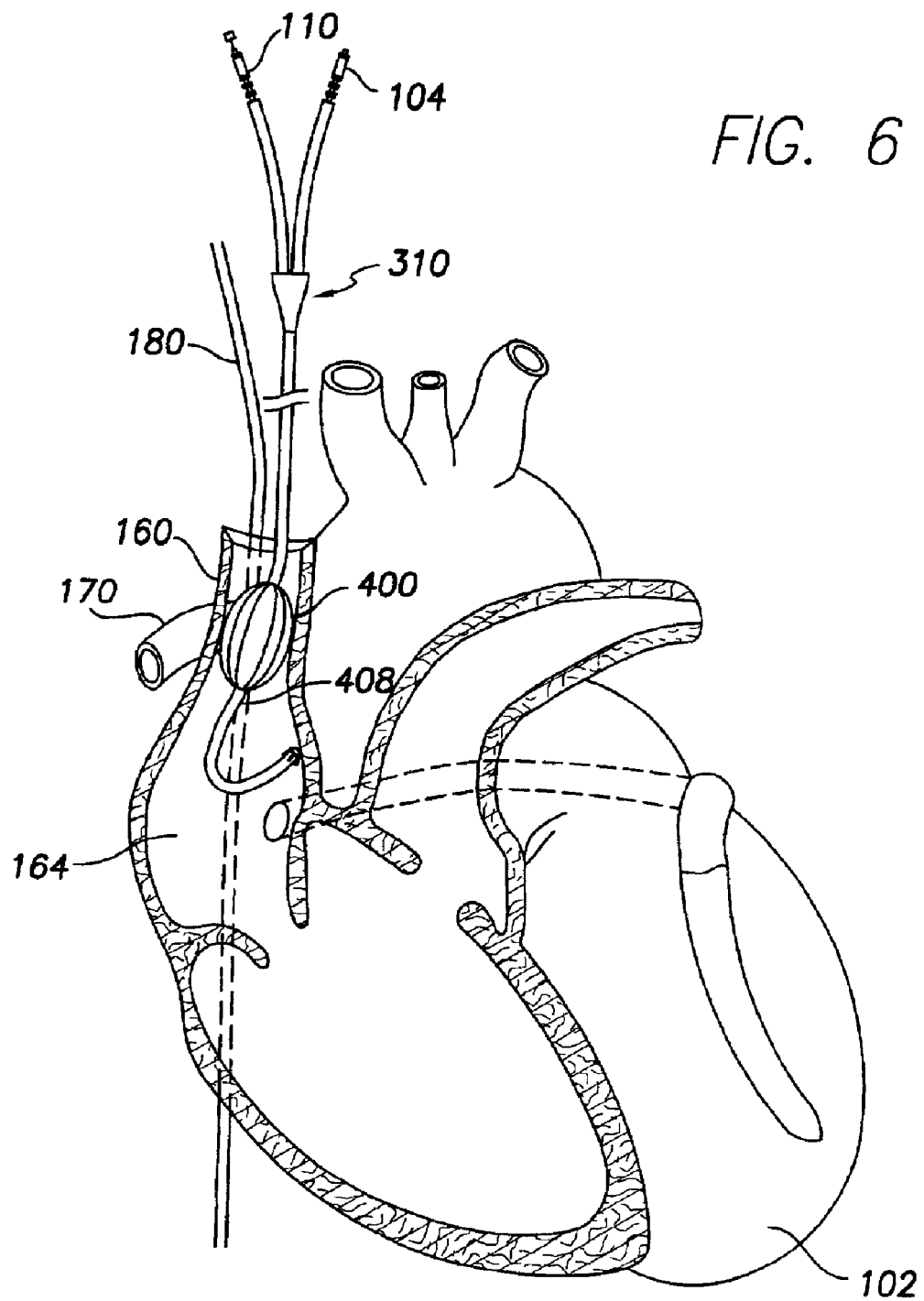

FIG. 6 is a dedicated right atrial lead 310 forming an conventional atrial-J configuration suitable for making contact to the right atrial connection 104 (i.e., a proximal connector coupled to a conductor) in addition to a vagal connection 110 (i.e., shown here for simplicity as a separate proximal connector coupled to a conductor). As shown in this embodiment, the vagal connection 110 is coupled to a deployable electrode (e.g., a basket electrode in this embodiment), and a distal end 408 without the stabilizing tail portion, as described in more complete detail in conjunction with FIG. 12, which instead continues "in-line" to form the distal end of the lead body where a conventional atrial electrode is attached.

Figure 7:
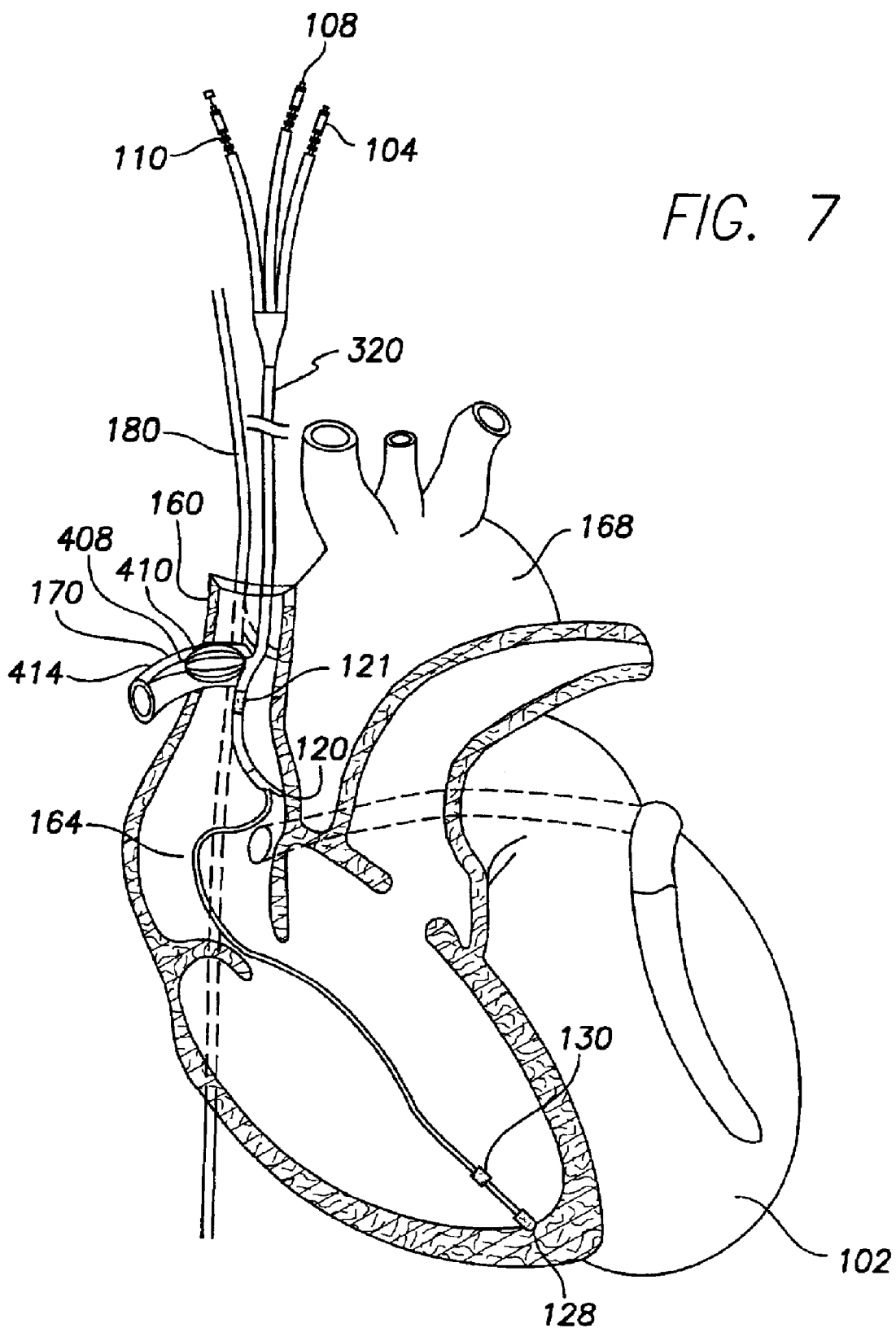

FIG. 7 illustrates a single-pass A-V lead 320 that combines the functions of the right atrial connection 104 and the left ventricular connection 108, and further adds a vagal connection 110 (i.e., shown here for simplicity as a separate proximal connectors coupled to a respective conductor). As shown in this embodiment, the vagal connection 110 is coupled to a deployable electrode (e.g., a basket electrode in this embodiment), and a distal end 408 with the stabilizing tail portion 414 (FIG. 12), and further includes atrial and ventricular pacing and sensing support using at least one ventricular electrode (128, 130, or both) and at least one atrial electrode (120, 121 or both). The advantages of the embodiment is that is supports A-V sensing, which is valuable for monitoring A-V dissociation (e.g., a partial or total interruption of the conduction from the atria to the ventricle, including prolongation of A-V conduction, first degree block (Mobitz I), second degree block (Mobitz II), or third degree A-V block) during vagal stimulation, as will be described in conjunction with the method steps in FIGS. 21–24

Figure 8:
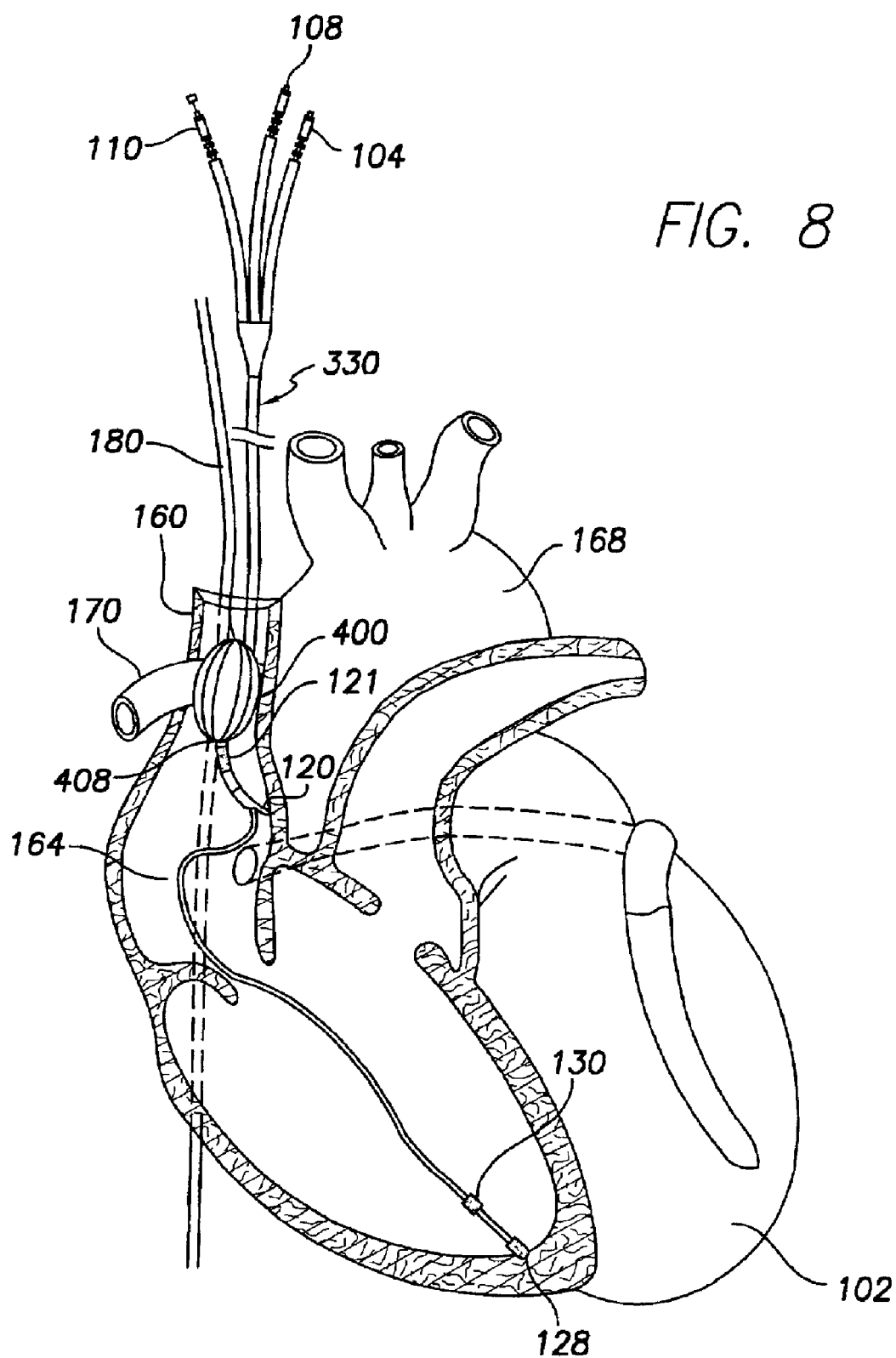

FIG. 8 illustrates a single-pass lead that combines the functions of the right atrial connection 104 and the left ventricular connection 108, with an "in-line" vagal connection 110. As shown in this embodiment, the vagal connection 110 is coupled to a deployable electrode (e.g., a basket electrode in this embodiment), and a distal end 408 (FIG. 11), which continues "in-line" to form at least one ventricular electrode (128, 130, or both) and at least one atrial electrode (120, 121 or both). In this embodiment, lead body between the atrial electrode 120 and the vagal electrode 400 (not shown to scale) may be configured to provide sufficient slack, or an atrial-J type shape, to allow placement of the atrial electrode 120 and further to allow the vagal electrode to be deployed against the SVC wall in a desired region near, or proximate, to the cardiac branch which will achieve a desired rate reduction by vagal stimulation.

Figure 9:
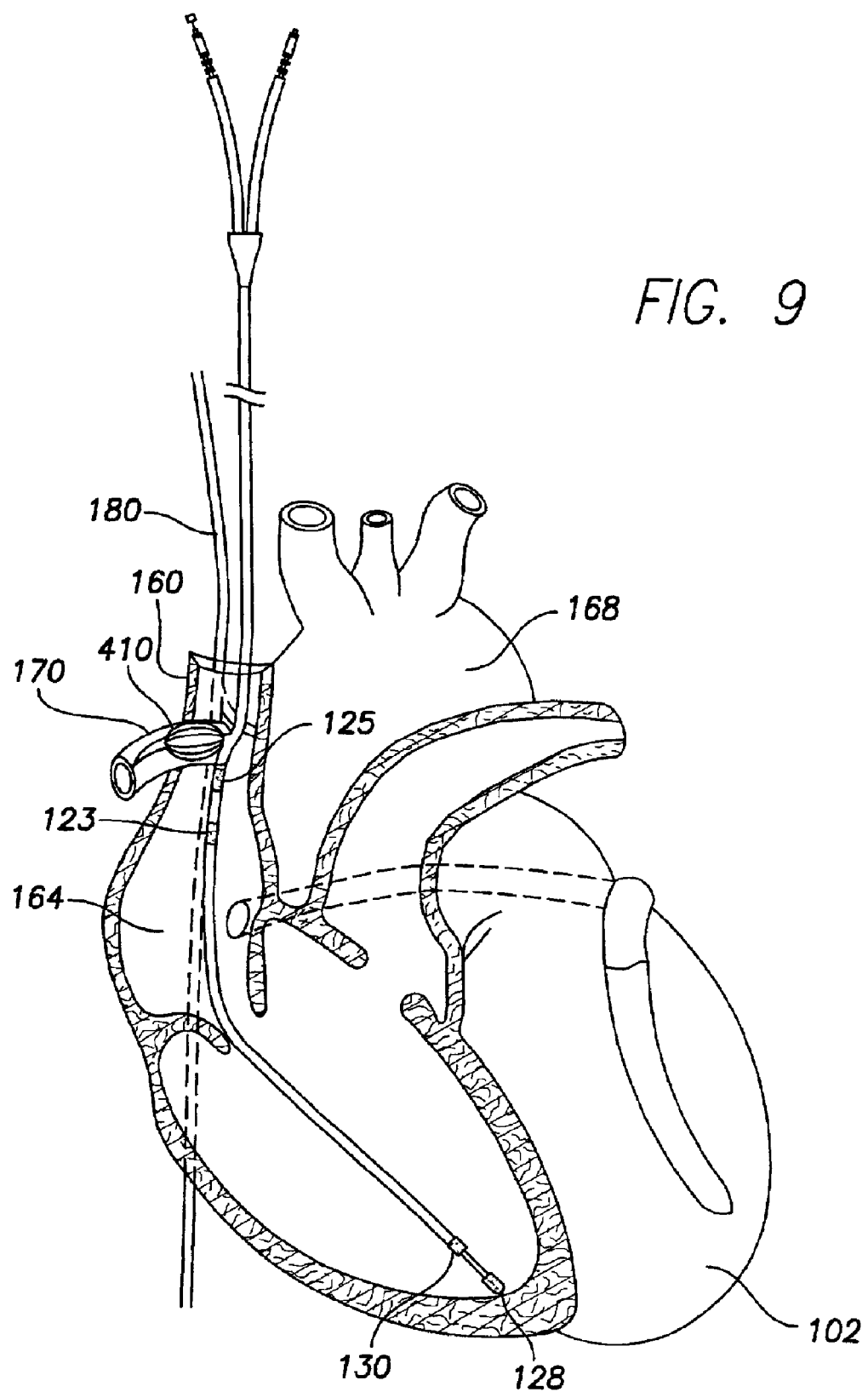

FIG. 9 illustrates yet another single-pass lead that combines the functions of the right atrial connection 104 and the left ventricular connection 108, with an "in-line" vagal connection 110. As shown in this embodiment, the atrial electrodes are shown as being conventional "in-line" ring electrodes (123, 125).

Figure 10:
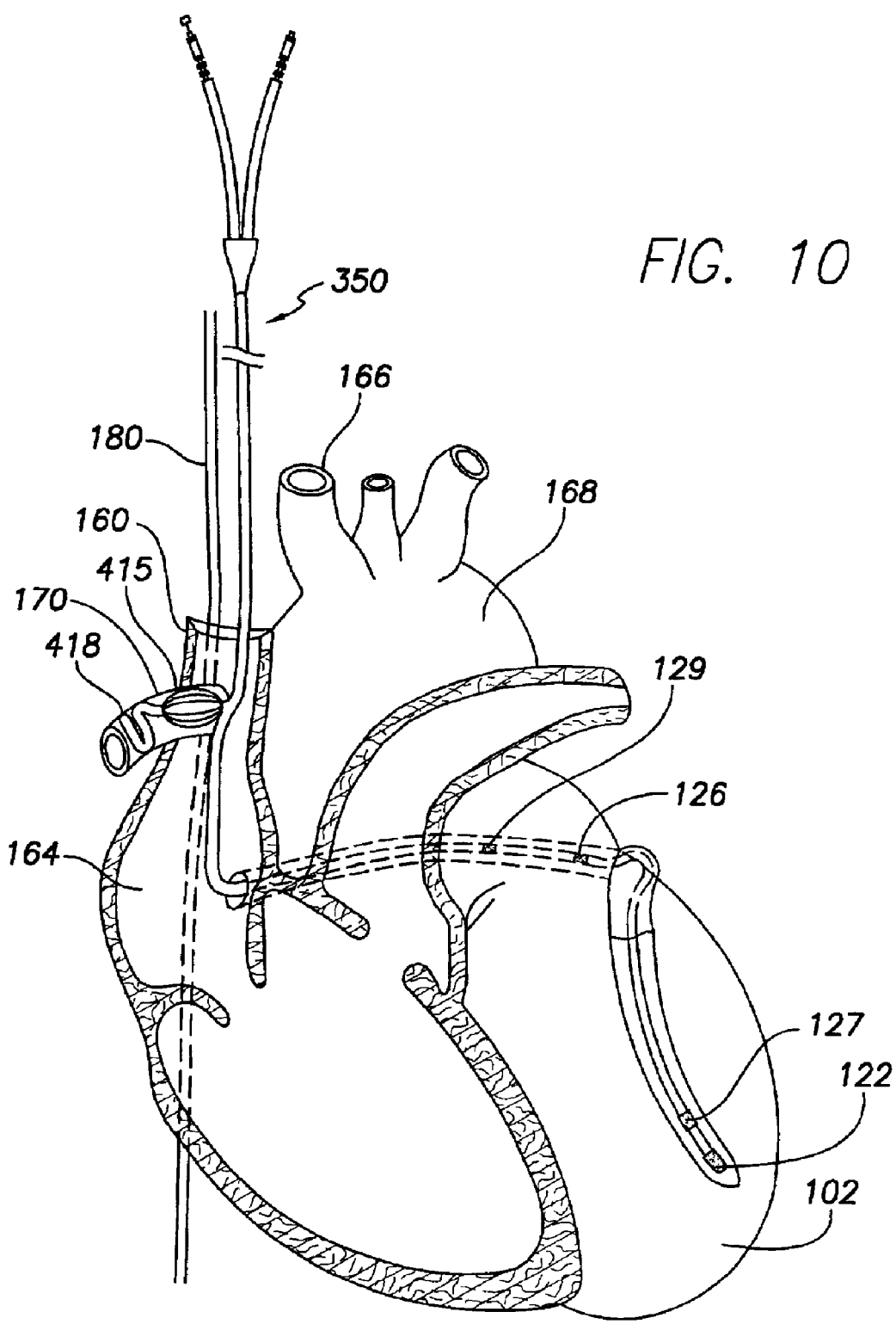

FIG. 10 illustrates a single-pass coronary sinus lead 350 that combines the functions of the coronary sinus connection 106 with a vagal connection 110. As shown in this embodiment, the vagal connection 1 10 is coupled to a deployable electrode (e.g., a basket electrode in this embodiment), and a distal end 408 having a stabilizing tail portion 416 in the shape of an "S" wiggle (as shown described in conjunction with FIG. 13). The lead 350 continues "in-line" to form at least one ventricular electrode (122, 127, or both) and optionally at least one atrial electrode (126, 129 or both). From the above description of the leads shown in FIGS. 6 and 8, it is within the spirit of the invention to include a vagal electrode to be deployed "in-line" against the SVC wall in a desired region near, or proximate, to the cardiac branch to also achieve the desired rate reduction by vagal stimulation.

While specific electrode combinations are shown, it is also within the spirit of the invention to add ring or coil electrodes in the atrium, or ventricle, or both and return electrodes in the SVC, as desired, to enhance tachyarrythmia therapy.

While specific stabilization techniques have been shown, a lead may include any stabilization technique, such as, a hook, a tine, a spiral and/or a wiggle for securing the lead in a vessel by actively or passively fixating or otherwise biasing against the vessel to anchor the lead into position. For example, a preformed "S" wiggle (such as the one disclosed in the U.S. patent application Ser. No. 09/457,254, previously incorporated by reference above) can secure a lead within a vessel by applying a force to bias against the vessel. The leads described herein optionally include at least one hook, tine, spiral, and/or wiggle.

FIGS. 11–15 show exemplary deployable or expandable electrode portions (400, 410, 415, 420, 440) suitable for use in the azygos vein. More specifically, the electrode portions (400, 420, 440) include a proximal portion (404, 424, 444) and a distal portion (408, 428, 448). Substantially positioned between the proximal portion (404, 424, 444) and the distal portion (408, 428, 448) is at least one electrode (416, 436, 456). Optionally, a shaft (412, 432, 452) may exist between the proximal or distal end to provide structural support. Alternatively, the electrodes (416, 436, 456) may be preshaped to attain their expanded state without a shaft.

Figure 12:
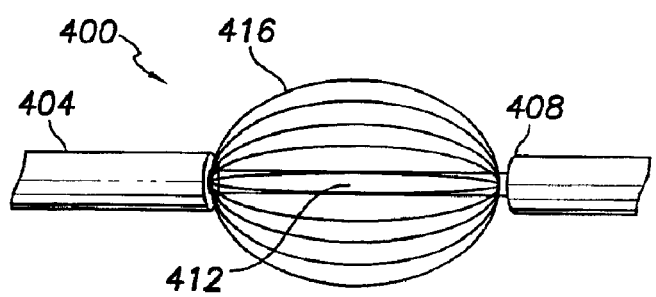
FIG. 12 is a side view diagram of another embodiment of a deployable electrode in the shape of a basket.
Figure 13:
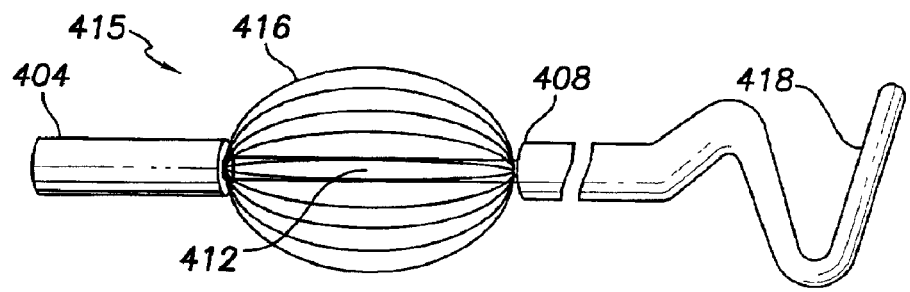
FIG. 13 is a side view diagram of another embodiment of a deployable electrode in the shape of a basket with a another type of stabilizing portion.

The electrode portion 400 shown in FIGS. 11–13 includes an electrode "basket" 416 or "basket electrode", which optionally includes more than one electrode. The basket electrode may be a length of exposed conductor, or individually placed electrodes, or an array of electrodes, as shown and described in U.S. Pat. Nos. 5,782,239 and 5,411,025, which patents are hereby incorporated by reference in their entirety. In one embodiment using the "side-arm" configuration (e.g., FIG. 7) in which the vagal electrode is place in the azygos vein rather than "in-line" near the SVC, an array of electrodes can be oriented or concentrated to face toward the tissue proximate to the cardiac branch. Upon implantation of such a lead, the side-arm and array of electrodes would self-orient towards the appropriate tissue.

Several methods, well known in the art, may be used to deploy the electrode portion. For example a stylet may be used to position the lead body into position and upon remove, the electrode will expand to its preformed shape. Alternately, a guiding sheath, or pull wire, may be used. For example, U.S. Pat. No. 5,411,025 discloses an outer catheter or sheath that holds the basket in its undeployed state during implant. U.S. Pat. No. 5,782,239 also discloses a puller wire which causes the basket to extend to its fully deployed state. These patents have already been incorporated herein by reference above. Balloon mechanisms/methods, expansion mechanisms/methods for expanding and/or securing leads are also known to one of ordinary skill in the art.

Figure 14:
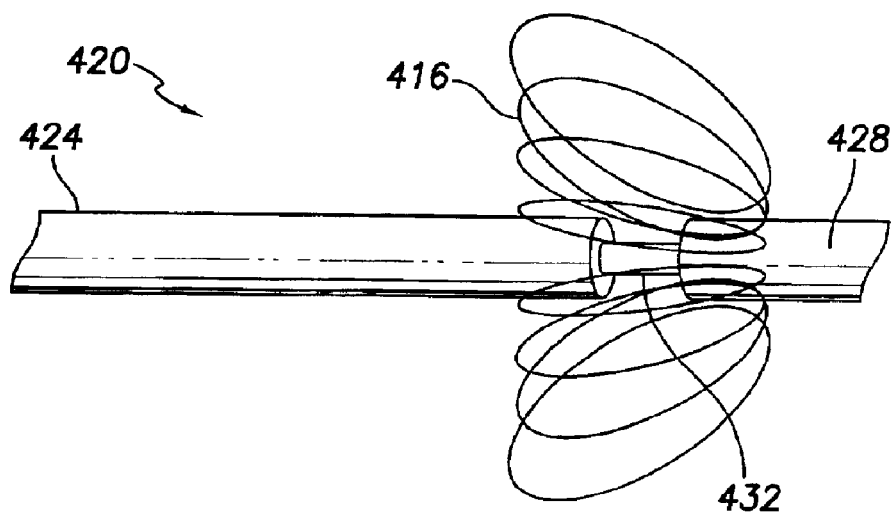
FIG. 14 is a side view diagram of another embodiment of a deployable electrode in the shape of an umbrella.

The electrode portion 420 shown in FIG. 14 includes an electrode "umbrella" 436 or "umbrella electrode", which optionally also includes more than one electrode (e.g., exposed conductors or an electrode array disposed thereon).

Figure 15:
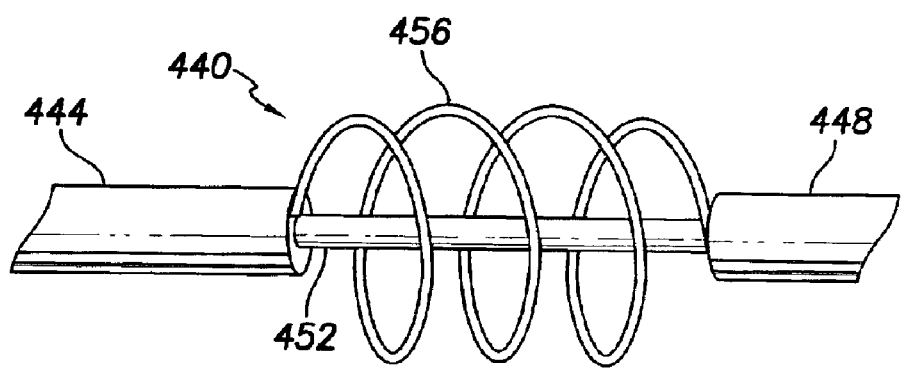
FIG. 15 is a side view diagram of yet another embodiment of a deployable electrode in the shape of a spiral.

The electrode portion 440 shown in FIG. 15 includes an electrode "spiral" 456 or "spiral electrode", which optionally includes more than one electrode (e.g. exposed conductors or an electrode array disposed thereon).

While three configurations have been disclosed (i.e., a basket, an umbrella, and a spiral electrode), these are for illustration purposes only as other deployable electrode configurations dimensioned to fit the desired location (e.g., azygos vein or SVC near the cardiac branch) are also possible.

Details of alternative "self-orienting" electrodes, are shown in FIGS. 16–19, that is, electrode configurations that would concentrate the current density in a direction towards the tissue adjoining the vagal and cardiac branch nerves.

FIGS. 16–17 show, in plan and axial cross-sectional views, an electrode portion 710 of a lead including an insulating tubing 720 includes three electrodes 712, 714, 716. According to an exemplary lead, the electrodes 712, 714, 716 have a fixed or fixable orientation with respect to the lead. The fixed or fixable orientation allows for electrode orientation prior to positioning of the lead in a patient's body or vein. Thus, according to this exemplary lead, the need to selectively employ electrodes to direct pulses applied to the electrodes to the desired nerve fibers or nerve regions is eliminated. As shown in FIG. 17, according to the exemplary fixed or fixable orientation lead, an electrode portion having, or using, only one or two of the three electrodes 712, 714, 716, allows for adequate vagal stimulation.

Figure 18:
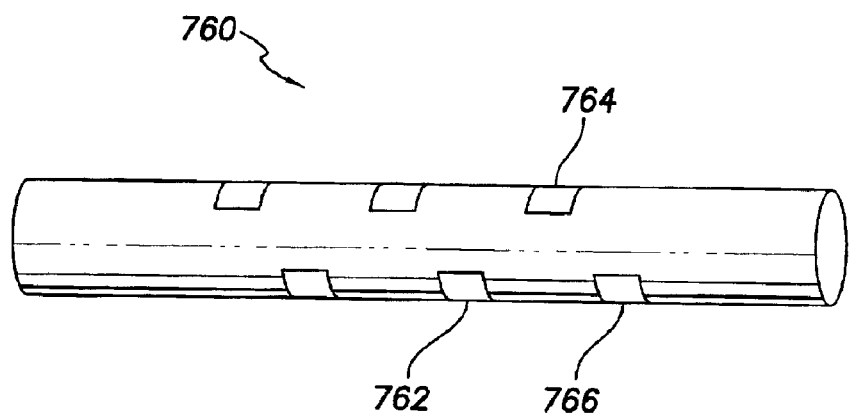
FIG. 18 is a side view diagram of another embodiment of a lead having another type of electrode array suitable for use with various leads and/or methods described herein.
Figure 19:
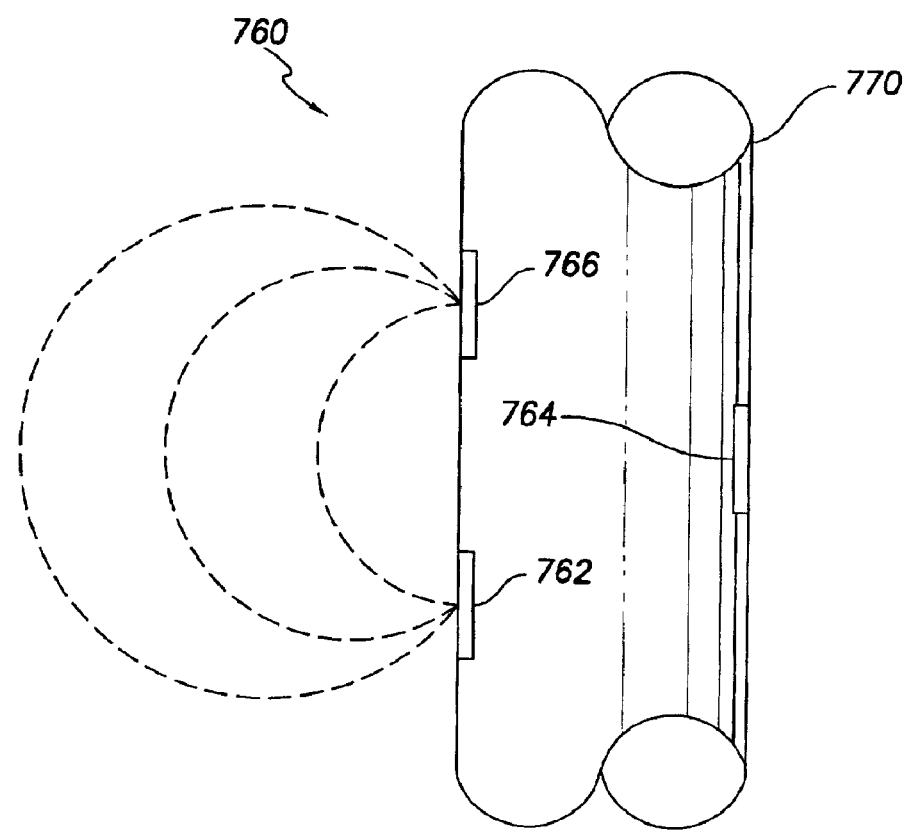
FIG. 19 is a side view diagram of the lead of FIG. 18 illustrating the current flow.

The same reasoning applies to the electrode portion 760 shown in FIGS. 18–19, which show, in plan and axial cross-sectional views, an electrode portion 760 of a lead including an insulating tubing 770 includes three electrodes 762, 764, 766.

A fixed or fixable lead and/or electrode portion orientation is achieved in a variety of manners. For example, consider a lead fixed or fixable for positioning in a patient's azygos vein 170. For example, the electrode portion 760 in shown in FIG. 20, and is placed in the azygos vein.

Figure 20:
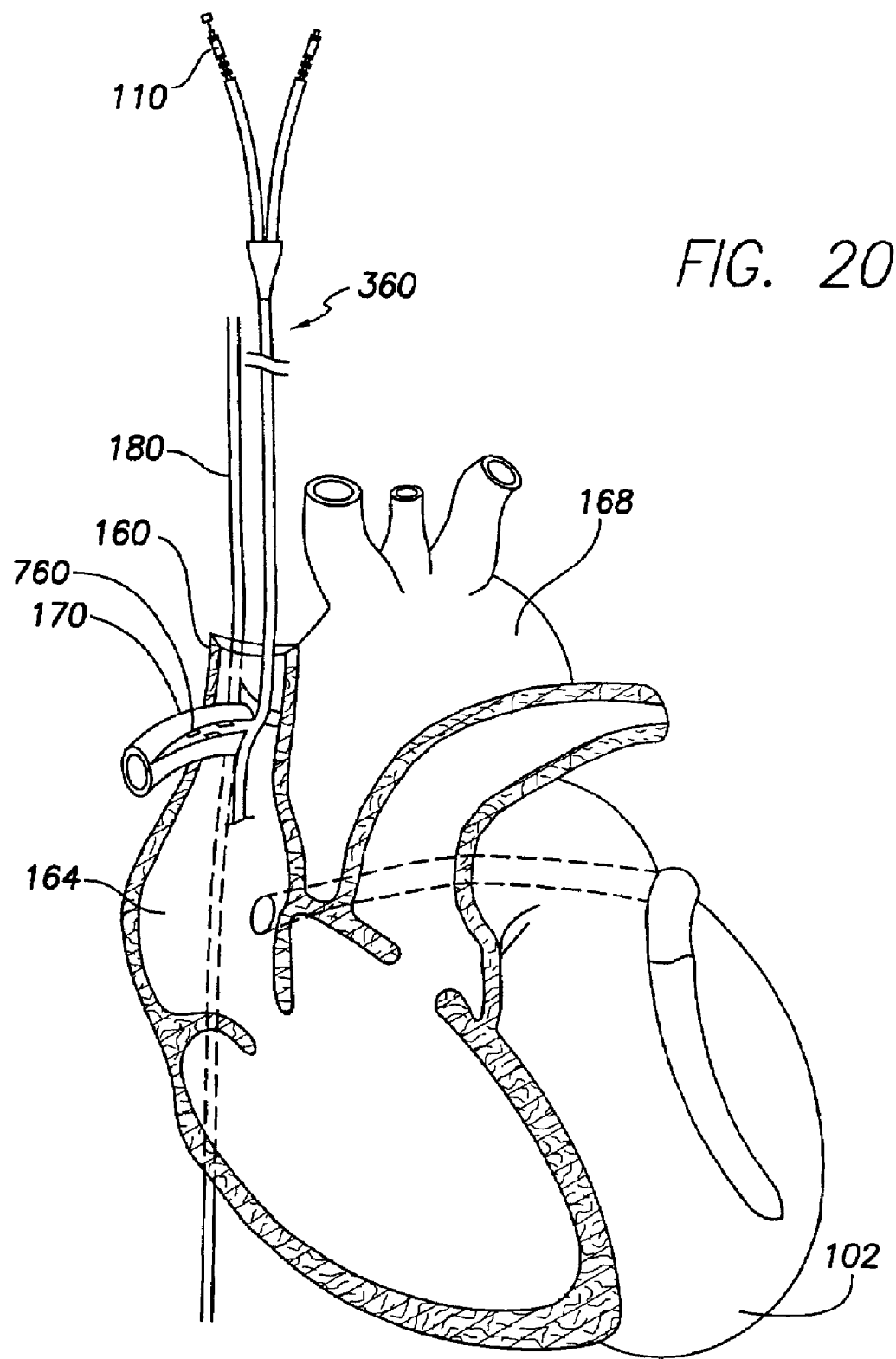
FIG. 20 illustrates the lead of FIGS. 18 and 19 as implanted near the vagal nerve through placement in or near the azygos vein in a location proximate to the vagal nerve and/or the cardiac branch.

FIG. 20 illustrates a single-pass lead 360 that combines the functions of the any desired connection (e.g., 104, 106 or 108) and with an "side arm" vagal connection 110. As shown in this embodiment, the vagal electrode is the electrode portion 760 shown in FIG. 18, but one of skill in the art could readily substitute the electrode portion 710 shown in FIG. 16. Accordingly, it can be appreciated that the electrodes can be oriented towards the tissue proximate to the vagal and cardiac branch nerves.

Thus, according to this example, the lead turns from the superior vena cava 160 to the azygos vein 170. The part of the lead that "turns" or extends into the azygos vein 160 allows for a fixed or fixable orientation.

The leads shown in FIGS. 7, 9 and 10 demonstrate other fixed or fixable orientation concept, referred to herein as a "side arm" as opposed to the aforementioned "turn". That is, the leads have fixed orientations due to at least one side arm. The side arm vagal portions dictate the orientation of their respective vagal portions in relation to the azygos vein. Thus, these side arm vagal portions also orient the vagal electrode portions in relation to the right vagus nerve and/or cardiac branch thereof.

For both the turn and side arm leads, the relatively short distance between (or including) the arch of the azygos vein 170 and the superior vena cava 160 allows for leads having an equally short vagal portion that is not particularly susceptible to twisting or misorientation. In other words, a turn lead having a vagal portion that is amenable to unpredictable twisting does not guarantee any reliable degree of orientation of a vagal portion electrode. Under such circumstances, an increase in vagal portion length generally increases the risk of misorientation. Thus, in general, a turn lead aids mainly in depth positioning and not necessarily in rotational positioning between the lead (e.g., vagal portion) and the walls of the vein. In this regard, a side arm lead can exhibit significant advantages over a turn lead.

Referring to FIG. 20, the vagal portion 760 includes electrode portions such as those shown in FIG. 19. According to this example, the side arm orients the electrode portion(s), preferably to alleviate the need to selectively employ electrodes to direct pulses applied to the electrodes to the desired nerve fibers or nerve regions. For example, referring to FIG. 17, the position of electrodes 712, 714, and 716 with respect to the azygos vein and right vagus nerve is generally known. With such information, a device may be configured to use only the electrodes facing the vagus nerve. Referring to FIG. 19, the orientation of electrodes 762, 764, 766 with respect to the azygos vein and right vagus nerve is known a priori. In addition, such an electrode portion may include taper or an "S" wiggle, wherein two electrodes 762, 766 are located on one side of the "S" and one electrode 764 is located on the other side of the "S". The a priori orientation information allows a device to be preprogrammed or wired to use only the electrodes can expect to achieve the most desirable pattern of nerve stimulation.

In yet another exemplary lead, an electrode portion optionally includes hooks, tines, and/or wiggles to orient and/or secure the vagal portion. Again, the use of hooks, tines, wiggles, and/or equivalents thereof alleviates the need to selectively employ electrodes to direct pulses applied to the electrodes to the desired nerve fibers or nerve regions.

FIGS. 5–10 and FIG. 20 show leads having a deployed electrode portion proximate to a distal portion positioned in a patient's superior vena cava 160. The position of the electrode portion in the superior vena cava 160 is proximate to the patient's right vagus nerve 180 and/or the cardiac branch 184 of the right vagus nerve 180. In these embodiment, the electrode portion appears in one of a location above the azygos vein 170, or in the superior vena cava 160 near the vagal nerves. Through such positioning, the electrode portion may stimulate the right vagus nerve 180, the cardiac branch 184 of the right vagus nerve 180, and/or a combination of both.

In any of the embodiment thus far described, the electrodes are implanted transvenously, in a undeployed state into a region proximate to the vagal nerves, and then deployed using conventional stylet, pull-wire, or guiding sheath. The lead may further contain, in a single-pass configuration, other electrodes for sensing and/or pacing and/or shock therapy to other chambers of the heart, as needed or desired.

Methods for Vagal Stimulation

The leads presented herein and equivalents thereof are suitable for stimulating a patient's vagus nerve. In an exemplary method, the method applies vagal stimulation of varying intensities until a desired reduced heart rate is achieved. In another embodiment, the method includes steps for automatically determining a parameter combination that defines the intensity (i.e., amplitude, pulse width and frequency) that achieves a desired reduced heart rate. In a further embodiment, the A-V conduction is monitored to ensure that A-V dissociation does not occur from too high an intensity of vagal stimulation.

And in still another embodiment, the power consumption is monitored and a plurality of parameter combinations that defines the intensity are tested to determine preferred combinations that do not draw too much current drain. Such a method optionally adjusts one or more of frequency, pulse width and/or amplitude of the stimulating. Such adjusting optionally occurs periodically during treatment of tachycardia and/or as part of a pre-treatment calibration sequence.

Advantageously, such methods of vagal stimulation will have a slowing effect on rate of sinus node depolarization and possible AV nodal conduction velocity which will aid in the control of heart rhythms and/or to aid in remodeling of the heart. In particular, control of the vagal tone can enhance tachycardia therapy.

An exemplary method responds to fast atrial rhythms such as pathological sinus tachycardia, atrial flutter, and atrial fibrillation by stimulating the right vagus nerve to slow a patient's heart sinus rhythm without causing A-V dissociation.

In any of the embodiments described below, upon detection of a high atrial rate, the system will deliver vagal stimulation through the deployed electrode to the vagal nerves by way of the right azygos vein. The system then check for an appropriate rate decrease, and further optimizes the appropriate stimulation level and further checks to see when the vagal stimulation is no longer needed. An exemplary method includes positioning an electrode portion of a lead in a patient's azygos vein and delivering an electrical signal to the electrode portion. In this exemplary method, the delivering optionally includes periodic delivery of an electrical signal having a desired magnitude. While fixed values may be programmed into the device based on implant testing, the present invention contemplates automatically determining an appropriate level of vagal stimulation by determining a level of amplitude, pulse width and frequency that are most effective in attaining the desired heart rate, and preferably can also optimize the current drain by determining the most efficient combination of amplitude, pulse width and frequency that attains the desired heart rate, as will be described below in conjunction with FIGS. 21–24.

Figure 21:
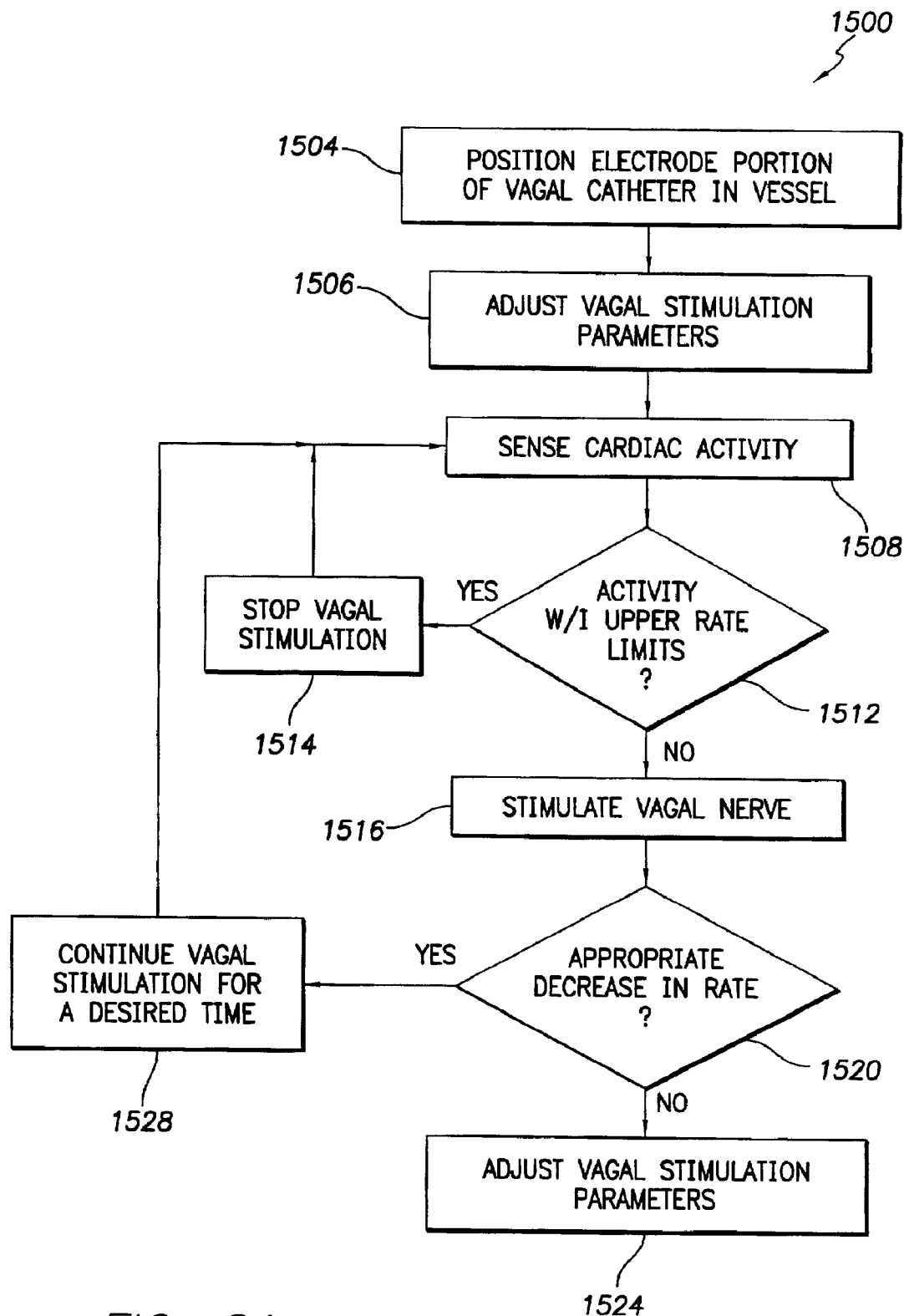
FIG. 21 is a functional block diagram of a method for stimulating a vagus nerve to slow heart rate when needed and automatically adjusting the stimulation intensity.

FIG. 21 shows a step diagram of an exemplary method 1500. A positioning step 1504 includes positioning of an electrode portion of a vagal lead in an appropriate vessel, such as, but not limited to, the azygos vein. An adjusting step 1506 adjusts vagal stimulation parameters (i.e., amplitude, pulse width and frequency), either manually or as described in more detail in FIG. 23. A sensing step 1508 senses cardiac activity, such as atrial heart rate. Next, a determination step 1512 determines whether the sensed cardiac activity is within desired limits. If yes at step 1512, then the method will disable vagal stimulation if it is currently turned on (at step 1514), and then returns to the sense step 1508 which continues senses cardiac activity. Thus, the sensing of heart rate within a normal range is determined by the determination step 1512 periodically (or continuously).

If the sensed cardiac activity is not within the limits at step 1512, then a stimulation step 1516 causes stimulation of the vagus nerve. A determination step 1520 follows to determine if the vagal nerve stimulation causes an appropriate decrease in heart rate, e.g., a rate decrease by approximate ½ the previous rate or simply a rate decrease in the normal range. If a decrease in heart rate is detected in step 1520, then the method returns to the sensing step 1508.

If, on the other hand, a decrease in heart rate is not detected in step 1520, then an adjusting step 1524 further adjusts the vagal stimulation parameters and returns to the stimulation step 1516 and the determination step 1520. This process continues until a desired set of vagal stimulation parameters is found to achieve the desired heart rate.

Once the desired heart rate is achieved (yes, at the determination step 1520), then vagal stimulation will continue for a desired time period (step 1528) (other pacing and/or monitoring functions being performed in the background as needed) until it is time to test to see if the underlying rhythm has returned to normal (steps 1508 and 1512) and, if so, then vagal stimulation can be turned off at step 1514. Thus, vagal stimulation is provided "on demand", that is, only when needed.

Figure 22:
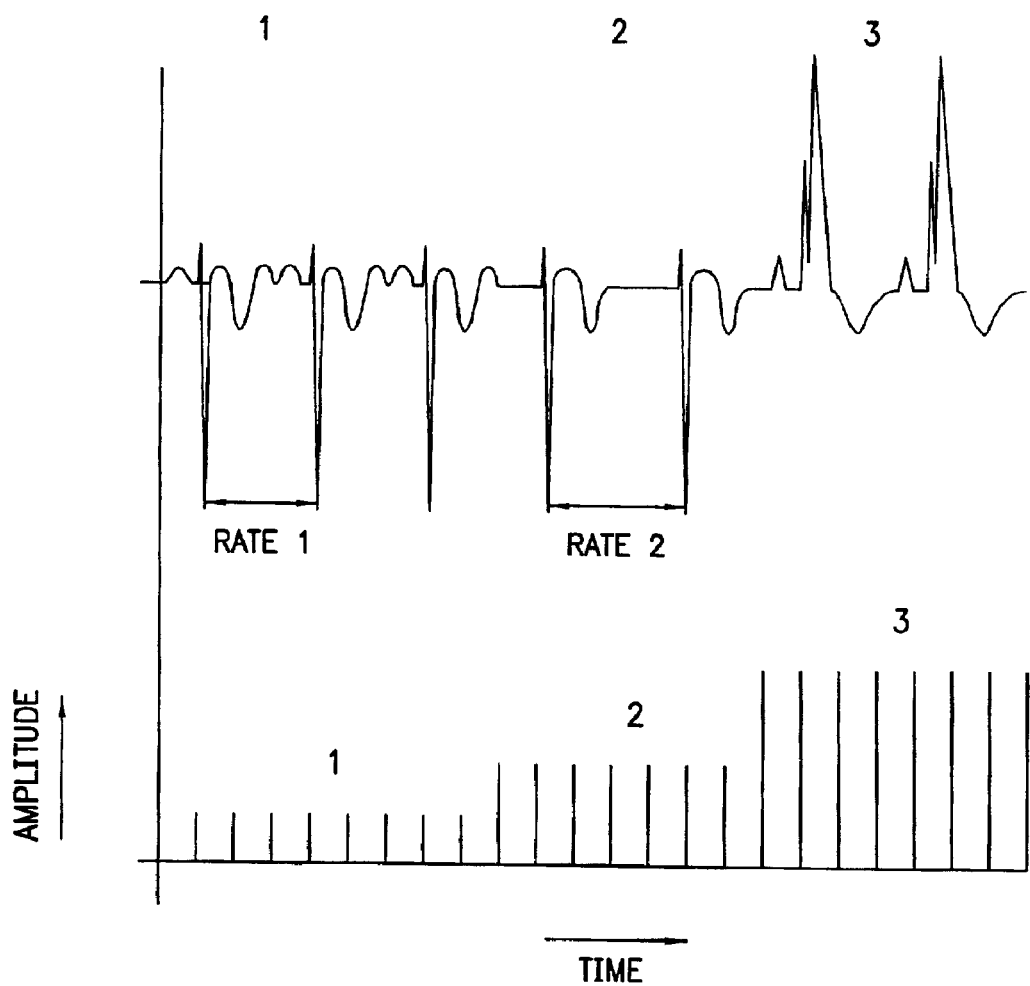
FIG. 22 is a plot of cardiac activity and pulse amplitude for vagal stimulation.

FIG. 22 illustrates several different responses to vagal stimulation. The upper plot shows cardiac activity with respect to time on a ECG strip while the lower plot shows vagal stimulation with respect to time. In both the upper and lower plots, three different segments, labeled I, II, and III, are shown. Rate I corresponds to tachycardia and vagal stimulation at a level that is insufficient to slow the rate. Rate II corresponds to a level of vagal stimulation that is sufficient to slow heart rate and eliminate tachycardia; thus, Rate II is less than Rate I. In the third segment, the level of vagal stimulation induces A-V dissociation which is observed on the ECG as being treated with backup ventricular pacing. For optimal results, vagal stimulation parameters should be adjustable to permit operation as shown in segment II.

Figure 23:
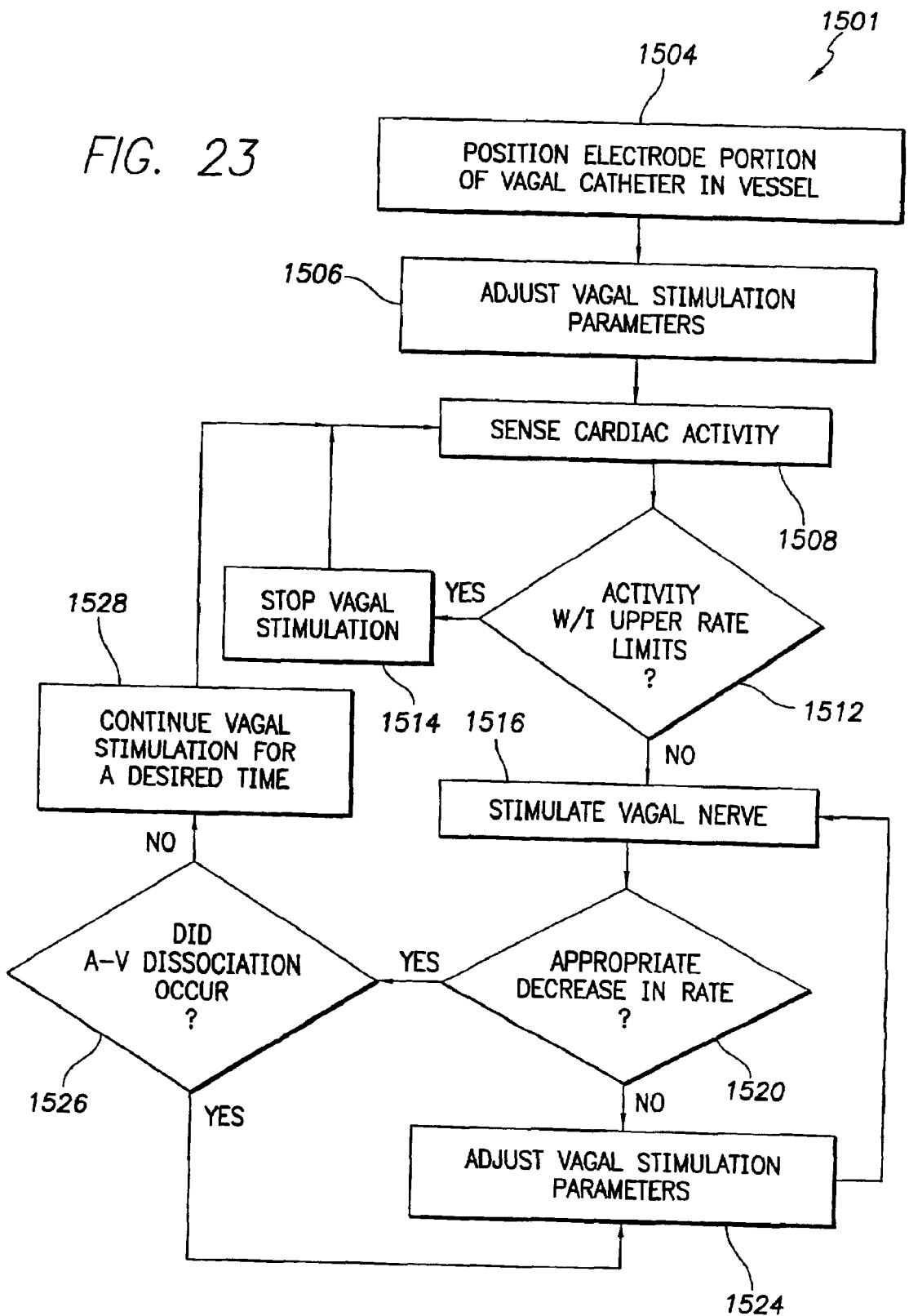
FIG. 23 is a functional block diagram of a method for adjusting vagal stimulation parameters when needed, and further automatically adjusting the stimulation intensity so as to prevent A-V dissociation (e.g., a partial or total interruption of the conduction from the atria to the ventricle, including prolongation of A-V conduction, first degree block (Mobitz I), second degree block (Mobitz II), or third degree (complete) A-V block)

FIG. 23 shows an exemplary method 1501 for adjusting vagal stimulation parameters to prevent A-V dissociation. The method proceeds with the same method as described above in FIG. 21 (like numbers being used throughout) until the determination step 1520.

As described with reference to FIG. 22, a given parameter combination that defines the intensity of the vagal stimulation may produce: (I) no decrease in heart rate; (II) a decrease in heart rate; or (III) A-V dissociation. If a decrease in heart rate has not occurred at step 1520, then further adjustment (e.g., increase) of a parameter or parameters is warranted, at the adjusting step 1524.

If the determination step 1520 detects a decrease in heart rate, then the method, at step 1526, determines whether A-V dissociation has occurred. If A-V dissociation has occurred, then further adjustment (e.g., a decrease) of a parameter or parameters is warranted, i.e., back to a level that did not cause A-V dissociation, at the adjusting step 1524. If A-V dissociation has not occurred at step 1526, then the method continues as described above to continue providing vagal stimulation only when needed (i.e., on demand) and at a level that does not incur A-V dissociation.

Figure 24:
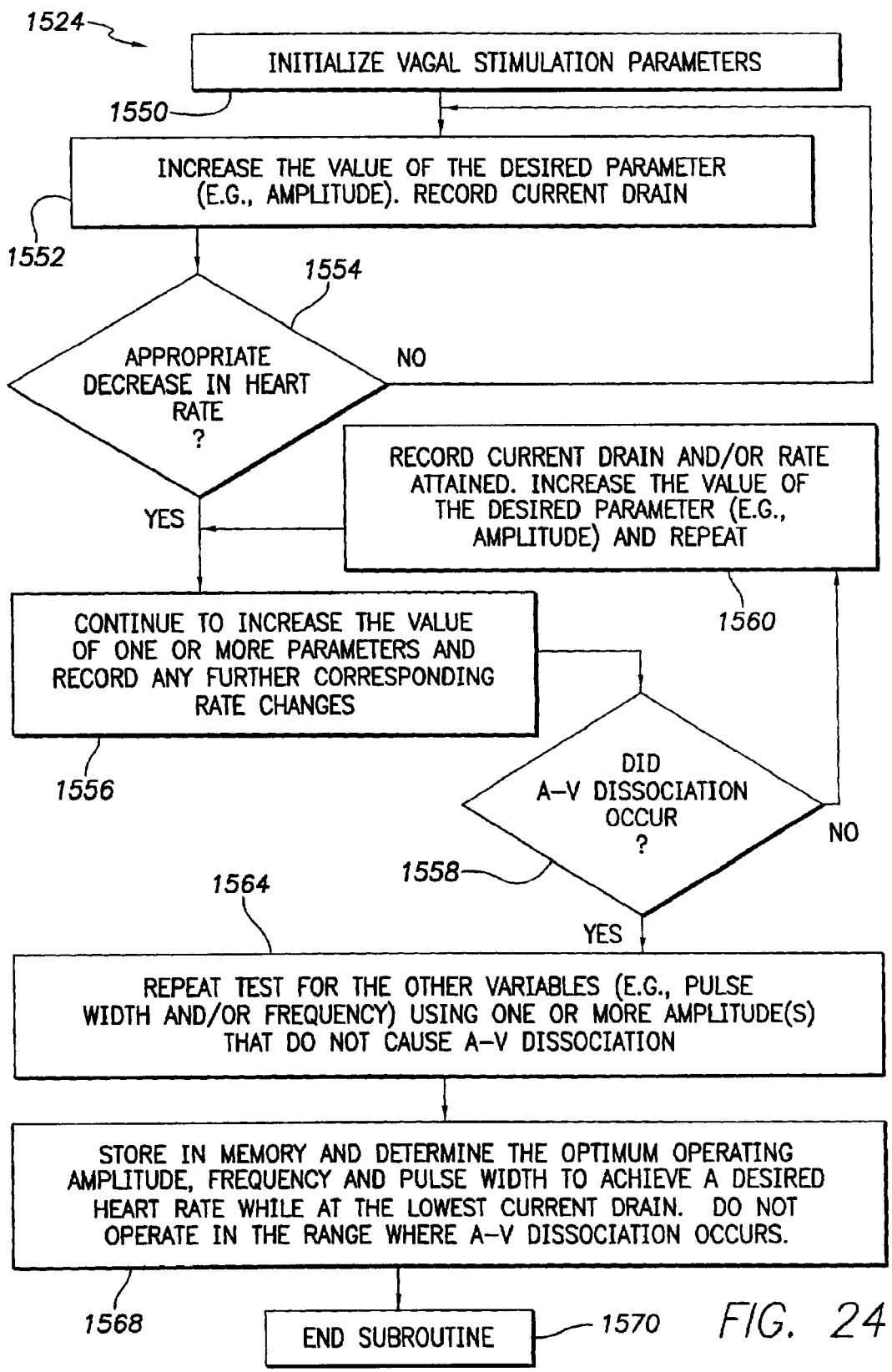
FIG. 24 is a functional block diagram of a more detailed exemplary method for automatically adjusting the stimulation intensity.

FIG. 24 shows an exemplary subroutine for step 1524 for adjusting vagal stimulation parameters to prevent A-V dissociation and further for determining a set of parameters that reduces, or minimizes, current drain. In the adjusting step 1524, a user and/or device adjusts a desired vagal stimulation parameter or parameters; such parameters include, but are not limited to, frequency, amplitude and pulse width.

The method begins at step 1550 with an initialization step, in which two parameters (e.g., frequency of stimulation and pulse width) may be set to a fixed values and a third parameter (hereinafter the "parameter under test", e.g., the amplitude) is initialized to a low value.

In step 1552, the value of the parameter under test (e.g., the amplitude) is then increased until a decrease in heart rate is detected in step 1554. If there has not been a heart rate decrease, then the parameter under test is further increased in step 1552.

If there has been a heart rate decrease at step 1554, then this is the lowest value for the parameter under test when used in combination with the fixed parameters. The method then may (optionally) proceed to step 1558 to further characterize the same parameter under test at higher values to determine if additional changes in rate can be obtained. Thus, a determination is made at step 1558 to verify that A-V dissociation has not occurred, and if not, then a recording step 1560 may record parameter values corresponding to the attained heart rate decrease, and/or power demand associated with vagal stimulation for the parameters.

The method may end here or, optionally, may continue to characterize the other two parameters (e.g., frequency or pulse width) in step 1564. The device may terminate the characterization once several combinations are found and it is apparent that at least one combination that achieves the desired heart rate and reduces current drain has been found.

Again, this particular method 1524 aims to adjust vagal stimulation parameters to decrease heart rate without causing A-V dissociation. The device can then operate using the set of parameters that reduces or minimizes current drain, thereby prolonging batter life.

The device 100 described with reference to FIG. 2 optionally implements aforementioned methods and leads. In particular, device 100 includes a vagal module 238 capable of performing a variety of tasks related to vagal stimulation.

As described herein an exemplary implantable stimulation lead has an electrode portion capable of stimulation of the right vagus nerve with leads to the heart for stimulating parasympathetic nerves for decreasing atrial heart rate (and preferably, without stimulating the phrenic nerve which can evoke undesirable diaphragmatic stimulation). One particular location of stimulation includes the cardiac branch site where the right vagus nerve enters into the right atrium at the level of the SVC/RA junction, or just below the azygos vein.

Other exemplary methods, described herein, include adjusting vagal stimulation until a desired reduction in atrial heart rate is achieved, while preserving sinus rhythm and A-V synchrony. In the event that provides backup A-V sequential support pacing is needed, the methods herein can be configured to do so in the event that asystole or A-V dissociation occurs.

One particular exemplary single-pass implantable stimulation lead can stimulate a desired portion of the right vagus nerve and stimulate the right atrium, the right ventricle and/or the left ventricle. Such leads optionally include an orientation which is generally known with reference to a patient's azygos vein, azygos arch, and/or hemiazygos veins.

Although the invention has been described in language specific to structural features and/or methodological acts, it is to be understood that the subject matter defined in the appended claims is not necessarily limited to the specific features or acts described. Rather, the specific features and acts are disclosed as exemplary forms of implementing the claimed invention.

What is claimed is:

1. A method for controlling a patient's heart rate, comprising:
    transvenously positioning a vagal electrode proximate to the patient's right vagus nerve near the patient's cardiac branch;
    positioning an atrial electrode in the patient's atrium;
    detecting the patient's atrial rate; and
    delivering stimulation pulses to the vagal electrode when a fast atrial rate is detected, the stimulation pulses being delivered at a level that reduces the atrial rate to a normal operating range.

2. The method of claim 1, wherein the delivering step comprises:
    adjusting the level of stimulation pulses so that the atrial rate decreases to a predetermined lower atrial rate.

3. The method of claim 2, wherein adjusting the level of stimulation pulses comprises:
    adjusting the level of stimulation pulses so that the atrial rate decreases to within a normal range.

4. The method of claim 2, wherein adjusting the level of stimulation pulses comprises:
    adjusting the level of stimulation pulses so that the atrial rate decreases to substantially half of the detected fast atrial rate.

5. The method of claim 2, wherein adjusting the level of stimulation pulses comprises:
    adjusting at least one of amplitude, pulse width and frequency.

6. The method of claim 2, further comprising:
    positioning a ventricular electrode in the patient's ventricle;
    monitoring A-V conduction intervals; and
    wherein the delivering step comprises delivering stimulation pulses at a level that does not cause A-V dissociation.

7. The method of claim 6, wherein the adjusting step further comprises:
    determining a plurality of operating parameter combinations that do not cause A-V dissociation, each combination including a stimulation pulse amplitude, frequency and pulse width;
    recording the resultant heart rate reduction for each combination; and
    wherein the delivering comprises delivering the stimulation pulses to the vagal electrode using the operating parameter combination that substantially achieves the predetermined lower atrial rate.

8. The method of claim 6, wherein the adjusting of the level of stimulation pulses further comprises:
    recording current drain for the plurality of operating parameter combinations that do not cause A-V dissociation; and
    wherein the delivering comprises delivering the stimulation pulses to the vagal electrode using the operating parameter combination that reduces the atrial rate without A-V dissociation and reduces current drain.

9. The method of claim 1, further comprising:
    periodically discontinuing delivering of the stimulation pulses to the vagal electrode;
    testing to determine if the atrial rate has returned to a normal range;
    disabling the delivery of the stimulation pulses to the vagal electrode when the atrial rate is in a normal range; and
    continuing the delivery of the stimulation pulses to the vagal electrode when the fast atrial rate is still present.

10. A method for controlling a patient's heart rate, comprising:
    positioning a vagal electrode proximate to the patient's right vagus nerve near the patient's cardiac branch;
    positioning an atrial electrode in the patient's atrium;
    detecting the patient's atrial rate; and
    delivering stimulation pulses to the vagal electrode when a fast atrial rate is detected, the stimulation pulses being delivered at a level that reduces the atrial rate to a normal operating range;
    wherein the delivering step comprises adjusting the level of stimulation pulses so that the atrial rate decreases to a predetermined lower atrial rate;
    wherein adjusting the level of stimulation pulses comprises adjusting at least one of amplitude, pulse width and frequency; and
    wherein adjusting of the level of stimulation pulses further comprises:
    testing a plurality of amplitude, pulse width and frequency combinations;
    recording current drain for the plurality of amplitude, pulse width and frequency combinations;
    determining at least one combination of amplitude, pulse width and frequency that reduces current drain; and
    delivering the stimulation pulses to the vagal electrode at a level that reduces the atrial rate to the predetermined lower rate while reducing current drain.

11. A method for controlling a patient's heart rate, comprising:
    positioning a vagal electrode proximate to the patient's right vagus nerve near the patient's cardiac branch;
    positioning an atrial electrode in the patient's atrium;
    detecting the patient's atrial rate; and
    delivering stimulation pulses to the vagal electrode when a fast atrial rate is detected, the stimulation pulses being delivered at a level that reduces the atrial rate to a normal operating range;

wherein the delivering step comprises adjusting the level of stimulation pulses so that the atrial rate decreases to a predetermined lower atrial rate;

wherein adjusting the level of stimulation pulses comprises adjusting at least one of amplitude, pulse width and frequency; and wherein adjusting of the level of stimulation pulses further comprises:

varying a plurality of amplitude, pulse width and frequency combinations to determine whether varying degrees of lower atrial rates can be achieved;

recording corresponding atrial rates for the plurality of amplitude, pulse width and frequency combinations; and selecting a particular amplitude, pulse width and frequency combination that corresponds to the predetermined lower atrial rate.

12. A method for controlling a patient's heart rate, comprising:

positioning a vagal electrode proximate to the patient's right vagus nerve near the patient's cardiac branch;

positioning an atrial electrode in the patient's atrium;

detecting the patient's atrial rate; and delivering stimulation pulses to the vagal electrode when a fast atrial rate is detected, the stimulation pulses being delivered at a level that reduces the atrial rate to a normal operating range;

wherein the positioning comprises positioning the vagal electrode in the right azygos vein.

13. The method of claim 12, wherein the positioning the vagal electrode in the right azygos vein comprises deploying an expandable vagal electrode configured to make contact with tissue proximate to the vagus nerve.

14. A method for controlling a patient's heart rate, comprising:

positioning a vagal electrode proximate to the patient's right vague nerve near the patient's cardiac branch;

positioning an atrial electrode in the patient's atrium;

detecting the patient's atrial rate; and delivering stimulation pulses to the vagal electrode when a fast atrial rate is detected, the stimulation pulses being delivered at a level that reduces the atrial rate to a normal operating range;

wherein the positioning comprises positioning the vagal electrode in the Superior Vena Cava (SVC) near the right cardiac branch.

15. The method of claim 14, wherein the positioning the vagal electrode in the SVC comprises deploying an expandable vagal electrode configured to make contact with tissue proximate to the vagus nerve and the right cardiac branch.

* * * * *